US010307491B2

(12) United States Patent
Moon et al.

(10) Patent No.: US 10,307,491 B2
(45) Date of Patent: Jun. 4, 2019

(54) LIPOSOMAL PARTICLES COMPRISING BIOLOGICAL MOLECULES AND USES THEREOF

(71) Applicant: THE REGENTS OF THE UNIVERSITY OF MICHIGAN, Ann Arbor, MI (US)

(72) Inventors: James Jaehyun Moon, Ann Arbor, MI (US); Yuchen Fan, Ann Arbor, MI (US); Preety Sahdev, Aliso Viejo, CA (US); Joseph Bazzill, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/547,389

(22) PCT Filed: Jan. 28, 2016

(86) PCT No.: PCT/US2016/015404
§ 371 (c)(1),
(2) Date: Jul. 28, 2017

(87) PCT Pub. No.: WO2016/123365
PCT Pub. Date: Aug. 4, 2016

(65) Prior Publication Data
US 2018/0021453 A1 Jan. 25, 2018

Related U.S. Application Data

(60) Provisional application No. 62/109,855, filed on Jan. 30, 2015.

(51) Int. Cl.
*A61K 9/127* (2006.01)
*A61K 47/69* (2017.01)
(Continued)

(52) U.S. Cl.
CPC ........ *A61K 47/6911* (2017.08); *A61K 9/1271* (2013.01); *A61K 9/0043* (2013.01);
(Continued)

(58) Field of Classification Search
CPC ..................................................... A61K 9/127
See application file for complete search history.

(56) References Cited

U.S. PATENT DOCUMENTS 8,598,339 B2   12/2013   Timmermann et al.
8,747,869 B2*  6/2014    Irvine ................. A61K 9/1273
                                                                   424/400
(Continued)

FOREIGN PATENT DOCUMENTS

EP         0092453       9/1987
WO         03/099261     12/2003
(Continued)

OTHER PUBLICATIONS

Banchereau J, et al., "Dendritic cells as therapeutic vaccines against cancer." Nat Rev Immunol. 2005;5(4):296-306.
(Continued)

*Primary Examiner* — Gollamudi Kishore
(74) *Attorney, Agent, or Firm* — Casimir Jones, S.C.

(57) ABSTRACT

Provided herein are liposomal particles. In particular, provided herein are liposomal particles comprising molecules (e.g., antigens or drugs) and uses thereof (e.g., as a vaccine (e.g., intranasal vaccine) or drug delivery system). For example, in some embodiments, the present disclosure provides a composition comprising: a molecule encapsulated in a liposome comprising one or more cationic lipids and hyaluronic acid (HA). In some embodiments, the one or more lipids are DOTAP and/or DOPE. In some embodiments, the HA is thiolated. In some embodiments, the thiolated HA is conjugated to thiolated PEG.

8 Claims, 18 Drawing Sheets

(51) Int. Cl.

| | |
|---|---|
| A61K 9/00 | (2006.01) |
| A61K 47/60 | (2017.01) |
| A61K 31/722 | (2006.01) |
| A61K 31/728 | (2006.01) |
| A61K 47/10 | (2017.01) |

(52) U.S. Cl.
CPC .......... *A61K 31/722* (2013.01); *A61K 31/728* (2013.01); *A61K 47/10* (2013.01); *A61K 47/60* (2017.08)

(56) References Cited

U.S. PATENT DOCUMENTS

| | | | |
|---|---|---|---|
| 2002/0012998 | A1 | 1/2002 | Gonda et al. |
| 2003/0008827 | A1 | 1/2003 | Dasseux et al. |
| 2004/0157253 | A1 | 8/2004 | Xu et al. |
| 2005/0226950 | A1 | 10/2005 | Sangwan |
| 2006/0154867 | A1 | 7/2006 | Sokoloff et al. |
| 2007/0110813 | A1 | 5/2007 | Ingenito et al. |
| 2009/0104268 | A1 | 4/2009 | Himmler et al. |
| 2009/0209458 | A1 | 8/2009 | Hawiger et al. |
| 2011/0065644 | A1 | 3/2011 | Xiet et al. |
| 2011/0305719 | A1 | 12/2011 | Naziruddin et al. |
| 2012/0016009 | A1 | 1/2012 | Fitzgerald et al. |
| 2012/0021050 | A1 | 1/2012 | Zhou et al. |
| 2012/0129916 | A1 | 5/2012 | Peer |
| 2012/0196815 | A1 | 8/2012 | Timmermann |
| 2012/0232005 | A1 | 9/2012 | Dasseux et al. |
| 2013/0034599 | A1 | 2/2013 | Thaxton et al. |
| 2013/0197055 | A1 | 8/2013 | Kamens et al. |
| 2014/0038894 | A1 | 2/2014 | Corrigan et al. |
| 2014/0045950 | A1 | 2/2014 | Lacko et al. |
| 2014/0121263 | A1 | 5/2014 | Fitzgerald et al. |
| 2014/0199241 | A1 | 7/2014 | Yedgar |
| 2014/0271827 | A1* | 9/2014 | Irvine ............... A61K 9/1273 424/450 |
| 2014/0356414 | A1* | 12/2014 | Wang ................ A61K 31/713 424/450 |
| 2016/0101170 | A1 | 4/2016 | Hacohen et al. |

FOREIGN PATENT DOCUMENTS

| | | |
|---|---|---|
| WO | 2004/018066 | 3/2004 |
| WO | 2012/149563 | 11/2012 |
| WO | 2013/126776 | 8/2013 |
| WO | 2015/034360 | 3/2015 |
| WO | 2016/011049 | 1/2016 |

OTHER PUBLICATIONS

Chen et al. "Enhanced Nasal Mucosal Delivery and Immunogenicity of Anti-Caries DNA Vaccine through Incorporation of Anionic Liposomes in Chitosan/DNA Complexes" PLOS One, Aug. 2013, vol. 8, Issue 8, 1-13.

Eliaz et al., "Liposome-encapsulated Doxorubicin Targeted to CD44" 2001, Cancer Res. 61:2592-2601.

Fan et al. "Cationic liposome-hyaluronic acid hybrid nanoparticles for intranasal vaccination with subunit antigens" Journal of Controlled Release, Apr. 11, 2015, vol. 208, pp. 121-129.

Holland et al., "Poly(ethylene glycol)—Lipid Conjugates Regulate the Calium-Induced Fusion of Liposomes Composed of Phosphatidylethanolamine and Phosphatidylserine" 1996, Biochem. 35:2618-2624.

Hutcheon et al., "Controlled destabilization of a liposomal drug delivery system enhances mitoxantrone antitumor activity." 1999, Biotechnol. 17:775-779.

International Search Report, International Patent Application No. PCT/US2016/015404, dated Apr. 11, 2016.

Matsuo K, et al., "A low-invasive and effective transcutaneous immunization system using a novel dissolving microneedle array for soluble and particulate antigens." J Control Release. 2012;161(1):10-7.

Mero et al. "Hyaluronic Acid Bioconjugates for the Delivery of Bioactive Molecules," Polymers, Jan. 30, 2014, vol. 3, pp. 346-369.

Moon et al. "Interbilayer-Crosslinked Multilameller Vesicles as Synthetic Vaccines for Potent Humoral and Cellular Immune Responses" Nat. Mater. Mar. 1, 2011, vol. 10, No. 3, pp. 243-251.

O'Brien et al., "Polymerization of Preformed Self-Organized Assemblies" 1998, Acc. Chem. Res. 31:861-868.

Papahadjopoulos D. et al., "Sterically stabilised liposomes: Improvements in pharmacokinetics, tissue disposition and anti-tumour therapeutic efficacy." 1991, Proc. Natl. Acad. Sci. 88:11460-11464.

Ruponen et al. "Interactions of polymeric and liposomal gene delivery systems with extracellular glycosaminoglycans: physicochemical and transfection studes" Biochimica et Biophysica Acta (1999) 1415, 331-341.

Saade F, et al., "A novel hepatitis B vaccine containing Advax, a polysaccharide adjuvant derived from delta inulin, induces robust humoral and cellular immunity with minimal reactogenicity in preclinical testing." Vaccine. 2013;31(15):1999-2007.

Sahdev et al. "Biomaterials for Nanoparticle Vaccine Delivery Systems," Pharm. Res. Oct. 16, 2014, vol. 31, No. 10, pp. 2563-2582.

Schmitz T, et al. "Synthesis and characterization of a chitosan-N-acetyl cysteine conjugate." Int J Pharm. 2008;347(1-2):79-85.

Silvius et al., "Interbilayer transfer of phospholipid-anchored macromolecules via monomer diffusion." 1993, Biochem. 32:3153-3161.

Torchilin, 2005, "Recent advances with liposomes as pharmaceutical carriers." Nat. Rev. Drug Discov. 4:145-160.

Ringsdorf et al., "Molecular Architecture and Function of Polymeric Oriented Systems: Models for the Study of Organization, Surface Recognition, and Dynamics of Biomembranes" 1988, Angew. Chem. Int. Ed. 27:113-158.

Ambardekar et al. "The Modification of siRNA with 3/ Cholesterol to Increase Nuclease Protection and Suppression of Native mRNA by Select siRNA Polyplexes" Biomaterials, Feb. 2011, vol. 32, No. 5, pp. 1-20.

Antipina, Maria N. et al. "Studies of nanoscale structural ordering in planar DNA complexes with amphiphilic mono- and polycations" Surface Science, 2003, vols. 532-535, pp. 1025-1033.

Fourcade, J. et al. "Immunization with analogue peptide in combination with CpG and Montanide expands tumor antigen-specific CD8+ T cells in melanoma patients" J. Immunother. 31, 781-791 (2008).

Ghaghada et al. "High-resolution Vascular Imaging of the Rat Spine Using Liposomal Blood Pool MR Agent" American Journal of Neuroradiology. Jan. 2007; vol. 28, No. 1; pp. 48-53, p. 48, col. 2, paragraph 2.

International Search Report & Written Opinion, International Patent Application No. PCT/US2016/024233, dated Aug. 29, 2016.

International Search Report & Written Opinion, International Patent Application No. PCT/US2017/014070, dated Aug. 3, 2017.

International Search Report & Written Opinion, International Patent Application No. PCT/US2017/038333, dated Nov. 24, 2017.

International Search Report & Written Opinion, International Patent Application No. PCT/US2017/040404, dated Feb. 2, 2016.

International Search Report, International Patent Application No. PCT/US2016/062250, dated Mar. 30, 2017.

Kreiter, S. et al. "Mutant MHC class II epitopes drive therapeutic immune responses to cancer" Nature 520, 692-696 (2015).

Marrache et al. Biodegradable Synthetic High-Density Lipoprotein Nanoparticles for Atherosclerosis, Proceedings of the Naitonal Academy of Sciences of the United States of America. May 13, 2013; vol. 110, No. 23, pp. 9445-9450.

Schumacher, T.N. & Schreiber, R.D. "Neoantigens in cancer immunotherapy." Science 348, 69-74 (2015).

Speiser, D.E. et al. "Rapid and strong human CD8+ T cell responses to vaccination with peptide, IFA, and CpG oligodeoxynucleotide 7909." J. Clin. Invest. 115, 739-746 (2005).

Yadav, M. et al. "Predicting immunogenic tumour mutations by combining mass spectrometry and exome sequencing." Nature 515, 572-576 (2014).

* cited by examiner

LIPOSOMAL PARTICLES COMPRISING BIOLOGICAL MOLECULES AND USES THEREOF

The present Application is a national phase application under 35 U.S.C. § 371 of PCT International Application No. PCT/US2016/015404, Jan. 28, 2016, which claims priority to U.S. Provisional Patent Application Ser. No. 62/109,855 filed Jan. 30, 2015 the disclosures of which is herein incorporated by reference in their entireties.

STATEMENT REGARDING FEDERALLY SPONSORED RESEARCH OR DEVELOPMENT

This invention was made with government support under AI097291 awarded by the National Institutes of Health. The Government has certain rights in the invention.

FIELD OF THE DISCLOSURE

Provided herein are liposomal particles. In particular, provided herein are liposomal particles comprising molecules (e.g., antigens or drugs) and uses thereof (e.g., as a vaccine (e.g., intranasal vaccine) or drug delivery system).

BACKGROUND OF THE DISCLOSURE

Liposomes are self-assembled vesicles having a spherical bilayer structure surrounding an aqueous core domain. Due to their intrinsic biocompatibility and ease of preparation, several liposomal drugs have been approved (Torchilin, 2005, Nat. Rev. Drug Discov. 4:145-160). In addition, modified liposomes on the nanoscale (20-200 nm) have been shown to have excellent pharmacokinetics profiles for the delivery of nucleic acids, proteins, and chemotherapeutic agents such as doxorubicin (Papahadjopoulos et al., 1991, Proc. Natl. Acad. Sci. 88:11460-11464; Eliaz et al., 2001, Cancer Res. 61:2592-2601). However, major drawbacks of liposome-based drug carriers include their instability and the lack of tunable triggers for drug release. As such, there have been several attempts at enhancing the properties of liposomes (Torchilin, 2005; Ringsdorf et al., 1988, Angew. Chem. Int. Ed. 27:113-158). Incorporation of polymerizable lipid amphiphiles leads to crosslinked liposomes with higher stability (O'Brien et al., 1998, Acc. Chem. Res. 31:861-868). Unfortunately, every lipid system would require a specific polymerizable amphiphile, making this approach synthetically cumbersome. In addition, the crosslinks are often too stable to allow for controllable release of the payload. To provide a combination of stability and modification generality, hydrophilic polymers such as poly(ethylene glycol) (PEG)(Papahadjopoulos et al., 1991) and poly (N-isopropylacrylamide)(Ringsdorf et al., 1988) have been added to liposomes. However, these modifiers can easily dissociate from the liposome surface, returning them to the unstable state (Adlakha-Hutcheon et al., 1999, Biotechnol. 17:775-779; Silvius et al., 1993, Biochem. 32:3153-3161; Holland et al., 1996, Biochem. 35:2618-2624).

As such, what are needed are liposomal constructs that will accommodate a wide variety of payloads (e.g., nucleic acids, peptides, small molecules, drugs, etc.), maintain stability, and deliver the payload to the intended location.

SUMMARY OF THE DISCLOSURE

Provided herein are liposomal particles. In particular, provided herein are liposomal particles comprising molecules (e.g., antigens or drugs) and uses thereof (e.g., as a vaccine (e.g., intranasal vaccine) or drug delivery system).

For example, in some embodiments, the present disclosure provides a composition comprising: a molecule encapsulated in a liposome comprising one or more cationic lipids and hyaluronic acid (HA). In some embodiments, the one or more lipids are DOTAP and/or DOPE. In some embodiments, the HA is thiolated. In some embodiments, the thiolated HA is conjugated to thiolated PEG. In some embodiments, the HA is present at a concentration of between 1 and 1000 µg HA per 1 mg of lipids. In some embodiments, the liposome further comprises an adjuvant (e.g., monophosphoryl lipid A (MPLA)). The present disclosure is not limited to particular molecules or agents for incorporating into liposomes. Examples include, but are not limited to, a protein, a peptide, a small molecule drug, an antibody, or a nucleic acid. In some embodiments, the composition further comprises a pharmaceutically acceptable carrier. In some embodiments, the molecule is an antigen.

Further embodiments provide a composition, comprising: a molecule encapsulated in a multilamellar lipid vesicle comprising covalent crosslinks between lipid bilayers, wherein at least two lipid bilayers in the multilamellar lipid vesicle are covalently crosslinked to each other by a thiolated biopolymer. In some embodiments, the lipid bilayers are crosslinked via functionalized lipids. The present disclosure is not limited to particular lipids. Examples include, but are not limited to, DOTAP, DOPE, DOBAQ, or DOPC. In some embodiments, the lipid is functionalized (e.g., with maleimide or dibenzocyclooctyne (DBCO)). The present disclosure is not limited to particular thiolated biopolymers. Examples include, but are not limited to, chitosan, polyglutamic acid, polyphosphazene, polyethyleneimine, polyalky acrylic acids (e.g. polymethylmethacrylate, poly(ethylacrylic acid), poly(propylacrylic acid), or poly(butylacrylic acid), HA, pegylated azide-modified polyethylenimine, branched polyethylenimine, or diazide). In some embodiments, the thiolated biopolymer comprises multiple sulfhydryl moieties. In some embodiments, the molecule comprises reactive thiols moieties (e.g., the molecule is conjugated to functionalized lipids in the lipid vesicle).

Additional embodiments provide methods and uses of delivering a molecule to a subject, comprising: administering any of the aforementioned compositions to a subject. In some embodiments, the molecule is an antigen and the administering induces an immune response to the antigen in the subject. In some embodiments, the immune response induces immunity against a pathogen or a tumor antigen.

Additional embodiments are described herein.

DEFINITIONS

Figure 1:
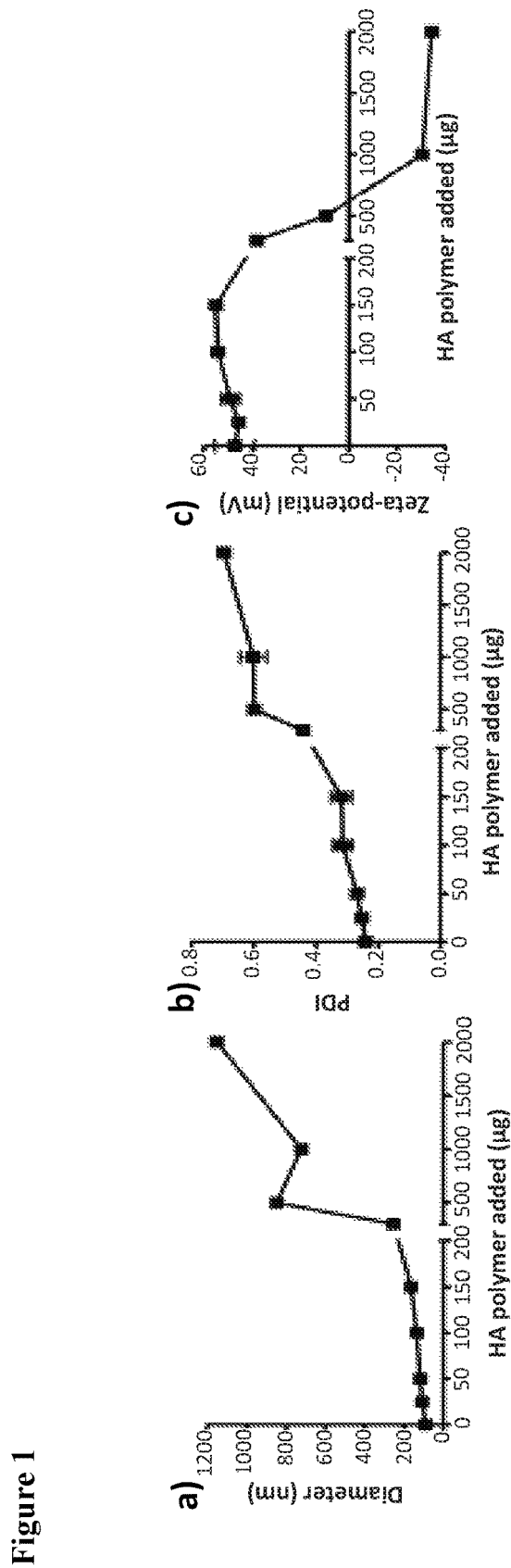
FIG. 1 shows characterization of liposomes interacting with varying amount of HA polymer. HA in varying amount (0, 25, 50, 100, 150, 300, 500, 1000, and 2000 µg) was added per 1 mg of DOTAP: DOPE liposomes, and particle size (a), PDI (b) and zeta potential (c) were measured.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "cell culture" or "tissue cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "payload" refers to any chemical entity, pharmaceutical, drug (such drug can be, but not limited to, a small molecule, an inorganic solid, a polymer, or a biopolymer), small molecule, nucleic acid (e.g., DNA, RNA, siRNA, etc.), protein, peptide and the like that is complexed with a liposomal formulation described in the present disclosure. A payload also encompasses a candidate (e.g., of unknown structure and/or function) for use to treat or prevent a disease, illness, sickness, or disorder of bodily function and includes, but is not limited to, test compounds that are both known and potential therapeutic compounds. A test compound can be determined to be therapeutic by screening using the screening methods of the present disclosure.

The term "nucleic acid" refers to a polymer of nucleotides, or a polynucleotide, as described above. The term is used to designate a single molecule, or a collection of molecules. Nucleic acids may be single-stranded or double-stranded, and may include coding regions and regions of various control elements, and are either deoxyribonucleotides or ribonucleotides.

The terms "protein" and "polypeptide" and "peptide" refer to compounds comprising amino acids joined via peptide bonds and are used interchangeably.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans). A used herein, the term "immune response" refers to a response by the immune system of a subject. For example, immune responses include, but are not limited to, a detectable alteration (e.g., increase) in Toll receptor activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to an agent (e.g., a microorganism (e.g., bacterium, virus or fungus) and/or portion or component thereof (e.g., a protein antigen)) that is capable of eliciting an immune response in a subject. In preferred embodiments, immunogens elicit immunity against the immunogen (e.g., microorganism (e.g., pathogen or a pathogen product)) when administered in combination with a composition described herein.

As used herein, the term "pathogen product" refers to any component or product derived from a pathogen including, but not limited to, polypeptides, peptides, proteins, nucleic acids, membrane fractions, and polysaccharides.

As used herein, the term "enhanced immunity" refers to an increase in the level of adaptive and/or acquired immunity in a subject to a given immunogen (e.g., microorganism (e.g., pathogen)) following administration of a composition (e.g., composition for inducing an immune response) relative to the level of adaptive and/or acquired immunity in a subject that has not been administered the composition (e.g., composition for inducing an immune response).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition described herein (e.g., a composition for inducing an immune response (e.g., a composition comprising a liposome or vesicle and an immunogen)) to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, etc.), topically, and the like.

As used herein, the terms "co-administration" and "co-administering" refer to the administration of at least two agent(s) (e.g., a composition comprising a lipsome or vesicle and an immunogen and one or more other agents—e.g., an adjuvant) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent. In other embodiments, co-administration is preferable to elicit an immune response in a subject to two or more different immunogens (e.g., microorganisms (e.g., pathogens)) at or near the same time (e.g., when a subject is unlikely to be available for subsequent administration of a second, third, or more composition for inducing an immune response).

As used herein, the term "topically" refers to application of a compositions described herein (e.g., a composition comprising a liposome or vesicle and an immunogen) to the surface of the skin and/or mucosal cells and tissues (e.g., alveolar, buccal, lingual, masticatory, vaginal or nasal mucosa, and other tissues and cells which line hollow organs or body cavities).

In some embodiments, the compositions are administered in the form of topical emulsions, injectable compositions, ingestible solutions, and the like. When the route is topical, the form may be, for example, a spray (e.g., a nasal spray), a cream, or other viscous solution (e.g., a composition comprising a lipsome or vesicle and an immunogen in polyethylene glycol).

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintigrants (e.g., potato starch or sodium starch glycolate), polyethylethe glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present disclosure that is physiologically tolerated in the target subject. "Salts" may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions with a suitable cation such as $Na^+$, $NH_4^+$, and $NW_4^+$ (wherein W is a $C_{1-4}$ alkyl group), and the like. For therapeutic use, salts are contemplated as being pharmaceutically acceptable. However, salts of acids and bases that are non-pharmaceutically acceptable may also find use, for example, in the preparation or purification of a pharmaceutically acceptable compound.

For therapeutic use, salts are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., age, environmental conditions, exposures to detrimental compounds present in the environment, etc.). Thus, it is not intended that the present disclosure be limited to any particular risk (e.g., a subject may be "at risk for disease" simply by being exposed to and interacting with other people), nor is it intended that the present disclosure be limited to any particular disease.

"Nasal application", as used herein, means applied through the nose into the nasal or sinus passages or both. The application may, for example, be done by drops, sprays, mists, coatings or mixtures thereof applied to the nasal and sinus passages.

As used herein, the term "kit" refers to any delivery system for delivering materials. In the context of immunogenic agents (e.g., compositions comprising a liposome or vesicle and an immunogen), such delivery systems include systems that allow for the storage, transport, or delivery of immunogenic agents and/or supporting materials (e.g., written instructions for using the materials, etc.) from one location to another. For example, kits include one or more enclosures (e.g., boxes) containing the relevant immunogenic agents and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a liposome or vesicle and an immunogen for a particular use, while a second container contains a second agent (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

The term "transfection" as used herein refers to the introduction of foreign nucleic acids (e.g., DNA or RNA) into eukaryotic cells. Transfection may be accomplished by a variety of means known to the art including, but not limited to, calcium phosphate-DNA co-precipitation, DEAE-dextran-mediated transfection, polybrene-mediated transfection, electroporation, microinjection, liposome fusion, liposomal, lipofection, protoplast fusion, retroviral infection, and biolistics. Embodiments of the present disclosure comprise liposomal transfection.

The term "about" as used herein (e.g. in references to a quantitative description), refers to +/−1-% (e.g., +/−10%, 9%, 8%, 7%, 6%, 5%, 4%, 3%, 2%, 1%, or fractions thereof).

As used herein, the term "microorganism" refers to any species or type of microorganism, including but not limited to, bacteria, viruses, archaea, fungi, protozoans, *mycoplasma*, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen," and grammatical equivalents, refers to an organism (e.g., biological agent), including microorganisms, that causes a disease state (e.g., infection, pathologic condition, disease, etc.) in another organism (e.g., animals and plants) by directly infecting the other organism, or by producing agents that causes disease in another organism (e.g., bacteria that produce pathogenic toxins and the like). "Pathogens" include, but are not limited to, viruses, bacteria, archaea, fungi, protozoans, *mycoplasma*, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent defect of the organism (e.g., genetic anomalies) or to combinations of these and other factors.

DETAILED DESCRIPTION OF THE DISCLOSURE

Provided herein are liposomal particles. In particular, provided herein are liposomal particles comprising molecules (e.g., antigens or drugs) and uses thereof (e.g., as a vaccine (e.g., intranasal vaccine) or drug delivery system).

In some embodiments, described herein is the synthesis of lipid-based nanoparticles (NPs) by inducing fusion of lipid vesicles with biodegradable polymer. For example, in some exemplary embodiments, cationic DOTAP-based liposomes were complexed with anionic hyaluronic acid-based biopolymers to promote fusion of liposomes into lipid-polymer hybrid NPs. The results indicated that these lipid-polymer hybrid NPs find use as a drug delivery platform and a vaccine delivery platform (e.g., for intranasal vaccination).

Embodiments of the present disclosure provide liposomes (e.g., encapsulating drugs or antigens). The present disclosure is not limited to particular liposomes. In some exemplary embodiments, liposomes comprising a lipid (e.g., cationic lipid) crosslinked with hyaluronic acid are provided. The present disclosure is not limited to particular lipids. Examples include, but are not limited to, DOTAP and DOPE (additional lipids are described below).

In some embodiments, liposomes comprise multilamellar lipid vesicles (MLV) (See e.g., U.S. Pat. No. 8,747,869; herein incorporated by reference in its entirety). Previously, a lipid-based nanoparticle system, called interbilayer-crosslinked multilamellar vesicles (ICMVs) that allow efficient encapsulation and sustained release of proteins for 30 days were described (Moon et al., Nat Mater 10, 243-251, 2011). Their potency as macromolecule delivery vehicles was demonstrated by delivering protein antigens in vivo, which significantly enhanced cellular and humoral immune responses compared to conventional vaccine systems. The "standard" ICMVs are crosslinked by DTT, which is a strong reducing agent that can reduce disulfide bonds in protein/peptide antigens, thus potentially disrupting 3D structure of encapsulated macromolecules. Another major limitations of ICMVs is that they are synthesized by linking phospholipids using bifunctional crosslinkers (resulting in only two phospholipid molecules crosslinked per one DTT molecule), which were identified as the major limiting factor in MVP stability. Provided herein are approaches to (1) avoid the use of reducing agent for synthesis of MVPs and (2) increase serum stability, thus achieving superior sustained release of cargo materials.

In some embodiments, MLV are stabilized by linking adjacent (or apposed) lipid bilayers to one another. As used herein, a multilamellar vesicle is a nano- or microsphere having a shell that is comprised of two or more concentrically arranged lipid bilayers. As used herein, adjacent or apposed lipid bilayers (or lipid bilayer surfaces) intend bilayers or surfaces that are in close proximity to each other but that are otherwise distinct and typically physically separate. This term does not typically mean the relationship between the two monolayers of a single bilayer.

In some exemplary embodiments, MLV are crosslinked with a thiolated biopolymer (e.g., HA), PEI-azide, branched PEI, or diazide via functionalized lipids (e.g., maleimide-functionalized lipids). In some embodiments, the lipids are one or more (e.g., 1 2, or 3) of DOTAP, DOBAQ, DOPE, DBCO, and DOPC. In some embodiments, the DOBAQ is maleimide-functionalized. In some embodiments, the lipids are modified with dibenzocyclooctyne (DBCO). In some embodiments, the thiolated biopolymer comprises multiple sulfhydryl moieties. In some embodiments, peptides (e.g., antigens) are linked to MLV via reactive thiols moieties coupled to functionalized lipids in the lipid vesicle.

In some embodiments, the present disclosure provides liposomes and vesicles encapsulating molecules. In some embodiments, the lipids and biopolymer have opposite charges. In some embodiments, lipids with functionalized headgroups are used to allow crosslinking with modified polymers. Exemplary lipids with cationic charges include, but are not limited to, 18:1 Dodecanyl PE (1,2-dioleoyl-sn-glycero-3-phosphoethanolamine-N-(dodecanyl)), 16:0 Succinyl PE (1,2-dipalmitoyl-sn-glycero-3-phosphoethanolamine-N-(succinyl)), 16:0 Glutaryl PE (1,2-dipalmitoyl-sn-glycero-3-phosphoethanolamine-N-(glutaryl)), and 18:1 Dodecanyl PE (1,2-dioleoyl-sn-glycero-3-phosphoethanolamine-N-(dodecanyl)). Lipids with anionic charges include, but are not limited to, 16:0 Dodecanylamine PE (1,2-dipalmitoyl-sn-glycero-3-phosphoethanolamine-N-(dodecanylamine)). Lipids with moieties reactive to sulfhydryl groups include but are not limited to, 16:0 MPB PE (1,2-dipalmitoyl-sn-glycero-3-phosphoethanolamine-N-[4-(p-maleimidophenyl)butyramide]), 16:0 PDP PE (1,2-dipalmitoyl-sn-glycero-3-phosphoethanolamine-N-[3-(2-pyridyldithio)propionate]), or 16:0 Ptd Thioethanol (1,2-Dipalmitoyl-sn-Glycero-3-Phosphothioethanol). Lipids with moieties reactive to streptavidin displaying groups include, but are not limited to, 16:0 Biotinyl PE (1,2-dipalmitoyl-sn-glycero-3-phosphoethanolamine-N-(biotinyl)). Lipids with moieties reactive to "click" chemistry include, but are not limited to, 16:0 azidocaproyl PE (1,2-dipalmitoyl-sn-glycero-3-phosphoethanolamine-N-(6-azidohexanoyl)).

Examples of polymers compatible with the fusion and crosslinking technology described herein include, but are not limited to, chitosan, polyglutamic acid, polyphosphazene, polyethyleneimine, polyalky acrylic acids (e.g. polymethylmethacrylate, poly(ethylacrylic acid), poly(propylacrylic acid), or poly(butylacrylic acid)).

Exemplary crosslinking methods compatible with the fusion and crosslinking technology described herein include, but are not limited to, sulfhydryl groups with maleimide, free thiol, or pyridyldithiol groups, amines with n-hydroxylsuccinimide groups, carboxylic acids with amines, and azides with alkynes.

The present disclosure is not limited to the specific lipids and vesicles described above. Additional MLV compositions are contemplated and are described herein.

In some embodiments described herein, covalent linkage between adjacent (or apposed) lipid bilayers in MLV is achieved through the use of crosslinkers and functionalized components of the lipid bilayer. The disclosure however contemplates that linking, including covalent linking, may be effected in other ways. As an example, the disclosure contemplates methods in which complementary reactive groups reside on components of adjacent bilayer surfaces and linkage between the bilayer surfaces is effected by reacting those groups to each other even in the absence of a crosslinker. Suitable complementary reactive groups are known in the art and described herein. The interior of the vesicle is typically an aqueous environment, and it may comprise an agent such as but not limited to a prophylactic, therapeutic or diagnostic agent. In some instances, the vesicles do not comprise a solid core, such as a solid polymer core (e.g., a synthetic polymer core). Instead, as discussed above, they may have a fluid core comprising agents of interest. The core may comprise monomers for polymerization into a hydrogel core in some instances. The vesicles may also be referred to herein as particles, including nano- or microparticles, although it is to be understood that such nano- or micro-particles have the attributes of the stabilized MLVs of the disclosure.

The amount of peptide or polypeptide (e.g., antigen) in the vesicles may vary and may depend on the nature of the peptide or polypeptide. For example, 300-400 µg of protein agent per mg of lipid may be incorporated into the vesicles. In some embodiments, the vesicles may comprise about 100 µg of agent, or about 150 µg of agent, or about 200 µg of agent, or about 250 µg of agent, or about 300 µg of agent, or about 325 µg of agent, or about 350 µg of agent, or about 375 µg of agent, or about 400 µg of agent, or about 410 µg of agent, per mg of lipid. In some embodiments, the agent may be a protein such as a protein antigen.

The diameter (e.g., mean diameter) of the vesicles may vary. In some instances, the vesicles will have a diameter ranging from about 100 to about 500 nm, including from about 125 to about 300 nm, including from about 150 to about 300 nm, including from about 175 to about 275 nm. In some instances, the diameter ranges from about 150 to about 250 nm. It will be understood that, in any preparation of vesicles, there will be heterogeneity between vesicles relating to vesicle diameter, number of lipid bilayers, amount of loaded agent, etc. Such distributions are shown in the Examples.

As used herein, the vesicles of the disclosure may also be referred to as liposomes (e.g., stabilized multilamellar liposomes or, as discussed below, interbilayer crosslinked multilamellar liposomes). Accordingly, the use of the term "vesicles" is not intended to convey source or origin of the vesicles. The vesicles of the disclosure are synthetic vesicles (i.e., they are produced in vitro), as will be discussed in greater detail below.

The vesicles may be isolated, intending that they are physically separated in whole or in part from the environment in which they are synthesized. As an example, vesicles comprising an agent (e.g., their "cargo" or "payload") may be separated in whole or in part from vesicles lacking agent (e.g., empty vesicles), and may then be referred to as "isolated vesicles." Separation may occur based on weight (or mass), density (including buoyant density), size, color and the like (e.g., where the cargo of the vesicle is detectable by its energy emission), etc. Centrifugation at about 14,000 g for about 4 minutes is sufficient to separate the vesicles, which pellet, from these other particle types.

The number of lipid bilayers in the stabilized multilamellar vesicles, may vary from about 2-30, but is more commonly in the range of 2-15. Accordingly, in various embodiments, the number of layers may be 2, 3, 4, 5, 6, 7, 8, 9, 10, 11, 12, 13, 14, 15 or more. The bilayers are typically comprised of lipids having hydrophilic heads and hydrophobic tails that are arranged in a manner similar to a cell membrane (i.e., with the hydrophilic heads exposed to typically an aqueous environment and the hydrophobic tails buried in the bilayer).

In some embodiments, vesicles are stabilized via crosslinks between their lipid bilayers, and they are therefore referred to as "interbilayer crosslinked" MLV. As used herein, this means that at least two lipid bilayers in the shell of the vesicle are crosslinked to each other. The crosslinked bilayers are typically those that are apposed or adjacent to each other. Most or all of the lipid bilayers in the shell may be crosslinked to their apposing lipid bilayer in the shell.

There may be one or more crosslinks between lipid bilayers. Typically, there will be numerous crosslinks between lipid bilayers. The arrangement and positioning of such crosslinks may be random or non-random. The degree of crosslinks (and thus the resultant stability of the vesicles) will depend upon the proportion of functionalized lipids (or other lipid bilayer components) used to make the vesicles and the crosslinking conditions (including, for example, time of incubation of the vesicles with a crosslinker). It will be understood that the higher the proportion of functionalized lipids (or other lipid bilayer components) in the vesicles, the more crosslinks that will be formed, all other factors and parameters being equal. Similarly, the more favorable the conditions towards crosslinking, the greater degree of crosslinking that will be achieved.

An exemplary synthesis method is as follows: Lipids and optionally other bilayer components are combined to form a homogenous mixture. This may occur through a drying step in which the lipids are dried to form a lipid film. The lipids are then combined (e.g., rehydrated) with an aqueous solvent. The aqueous solvent may have a pH in the range of about 6 to about 8, including a pH of about 7. Buffers compatible with vesicle fusion are used, typically with low concentrations of salt. The solvent used in the Examples is a 10 mM bis-tris propane (BTP) buffer pH 7.0. The nature of the buffer may impact the length of the incubation. For example, a buffer such as PBS may require a longer incubation time as compared to a buffer such as BTP, all other things being equal. If the buffer is PBS, then the incubation times may be about 6-24 hours, or 8-16 hours, or 10-12 hours. If the buffer is BTP, then the incubation times may be shorter including 1-4 hours, or 1-2 hours. Accordingly a variety of aqueous buffers may be used provided that a sufficient incubation time is also used. This step may also include the presence of the agent(s) to be incorporated into the vesicles. The resultant liposomes are then incubated with one or more divalent cations in order to fuse them into multilamellar vesicles. Suitable divalent cations include $Mg^{2+}$, $Ca^{2+}$, $Ba^{2+}$, or $Sr^{2+}$. Multivalent or polymeric cations could also be employed for vesicle fusion. Vesicle fusion could also be achieved via the mixing of cationic vesicles with divalent or higher valency anions; an example would be fusion of cationic liposomes with DNA oligonucleotides or DNA plasmids. This may be done under agitation such as sonication, vortexing, and the like. If the liposomes were made in the presence of an agent, the MLVs will comprise the agent in their core and/or between the concentrically arranged lipid bilayers. The disclosure contemplates fusion of liposomes carrying different agents to form MLVs that comprise such agents.

The resultant MLVs are then incubated with a crosslinker, and preferably a membrane-permeable crosslinker. As stated herein, the nature of the crosslinker will vary depending on the nature of the reactive groups being linked together. As demonstrated in the Examples, a dithiol-containing crosslinker such as DTT or (1,4-Di-[3'-(2'-pyridyldithio)-propionamido]butane) may be used to crosslink MLVs comprised of maleimide functionalized lipids (or other functionalized lipid bilayer components), or diazide crosslinkers could be used to crosslink alkyne headgroup lipids via "click" chemistry. These various incubations are all carried out under aqueous conditions at a pH in the range of about 6 to about 8, or about 6.5 to about 7.5, or at about 7. The crosslinking step may be performed at room temperature (e.g., 20-25° C.) or at an elevated temperature including for example up to or higher than 37° C.

The resultant crosslinked vesicles may then be collected (e.g., by centrifugation or other pelleting means), washed and then PEGylated on their outermost or external surface (e.g., as used herein, the vesicles may be referred to "surface-PEGylated" or "surface-conjugated" to PEG) by incubation with a thiol-PEG. The PEG may be of any size, including but not limited to 0.1-10 kDa, 0.5-5 kDa, or 1-3 kDa. A 2 kDa PEG functionalized with thiol is used in the Examples. The incubation period may range from about 10 minutes to 2 hours, although it may be shorter or longer depending on other conditions such as temperature, concentration and the like. The PEGylation step may be performed at room temperature (e.g., 20-25° C.) or at an elevated temperature including for example up to or higher than 37° C. A 30 minute incubation period is used in the exemplary synthesis methods of the Examples. The vesicles then may be collected (e.g., by centrifugation or other pelleting means) and washed with water or other aqueous buffer.

The vesicles may be stored at 4° C. in a buffered solution such as but not limited to PBS or they may be lyophilized in the presence of suitable cryopreservants and then stored at −20° C. Suitable cryopreservants include those that include sucrose (e.g., a 1-5% sucrose, and preferably about 3% sucrose solution).

Crosslinking could also be achieved by coupling between a reactive group in one bilayer with a complementary reactive group in the adjacent bilayer. For example, fused vesicles containing succinimidyl ester-functionalized lipid (A) headgroups and primary-amine-containing (B) headgroups could achieve crosslinking by in situ reaction between the A and B lipids of adjacent bilayers. A variety of other complementary functionalized lipids familiar to those skilled in the art could be employed in a similar manner.

The molar ratio of functionalized lipid (or other functionalized component of the lipid bilayer) to crosslinker may vary depending on the conditions. In some instances, it may range from about 1 to about 5. In some embodiments, a molar ratio of 2 is sufficient (e.g., the molar ratio of functionalized lipid (or component) to crosslinker is 2:1). The incubation time may range from 1 hour to 24 hours, from 2-18 hours, from 2 to 12 hours, or from 2 to 6 hours. In some instances, it may be about 2 hours. In other instances, it may be overnight (e.g., about 12 hours).

The molar % of the functionalized lipid in the vesicles may range from 1% to 100%, or from about 10% to about 60% in some instances, or from about 25% to about 55% in some instances. In some instances, the molar % of the functionalized lipid in the vesicles is typically at least 10%, preferably at least 15%, more preferably at least 20%, and even more preferably at least 25%.

Conversely, the non-functionalized lipids may be present at about 0% to 99% as a molar %. More typically, the non-functionalized lipids may be present at about 40%-75% or 40% to 60% as a molar %.

The vesicles are comprised of one or more lipids. The type, number and ratio of lipids may vary with the proviso that collectively they form spherical bilayers (e.g., vesicles). The lipids may be isolated from a naturally occurring source or they may be synthesized apart from any naturally occurring source.

In some embodiments, at least one (or some) of the lipids is/are amphipathic lipids, defined as having a hydrophilic and a hydrophobic portion (typically a hydrophilic head and a hydrophobic tail). The hydrophobic portion typically orients into a hydrophobic phase (e.g., within the bilayer), while the hydrophilic portion typically orients toward the aqueous phase (e.g., outside the bilayer, and possibly between adjacent apposed bilayer surfaces). The hydrophilic portion may comprise polar or charged groups such as carbohydrates, phosphate, carboxylic, sulfato, amino, sulfhydryl, nitro, hydroxy and other like groups. The hydrophobic portion may comprise apolar groups that include without limitation long chain saturated and unsaturated aliphatic hydrocarbon groups and groups substituted by one or more aromatic, cyclo-aliphatic or heterocyclic group(s). Examples of amphipathic compounds include, but are not limited to, phospholipids, aminolipids and sphingolipids.

Typically, the lipids are phospholipids. Phospholipids include without limitation phosphatidylcholine, phosphatidylethanolamine, phosphatidylglycerol, phosphatidylinositol, phosphatidylserine, and the like. It is to be understood that other lipid membrane components, such as cholesterol, sphingomyelin, cardiolipin, etc. may be used.

The lipids may be anionic and neutral (including zwitterionic and polar) lipids including anionic and neutral phospholipids. Neutral lipids exist in an uncharged or neutral zwitterionic form at a selected pH. At physiological pH, such lipids include, for example, dioleoylphosphatidylglycerol (DOPG), diacylphosphatidylcholine, diacylphosphatidylethanolamine, ceramide, sphingomyelin, cephalin, cholesterol, cerebrosides and diacylglycerols. Examples of zwitterionic lipids include without limitation dioleoylphosphatidylcholine (DOPC), dimyristoylphosphatidylcholine (DMPC), and dioleoylphosphatidylserine (DOPS). An anionic lipid is a lipid that is negatively charged at physiological pH. These lipids include without limitation phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

Collectively, anionic and neutral lipids are referred to herein as non-cationic lipids. Such lipids may contain phosphorus but they are not so limited. Examples of non-cationic lipids include lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, and cholesterol.

Additional nonphosphorous containing lipids include stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Lipids such as lysophosphatidylcholine and lysophosphatidylethanolamine may be used in some instances.

Noncationic lipids also include polyethylene glycol-based polymers such as PEG 2000, PEG 5000 and polyethylene glycol conjugated to phospholipids or to ceramides (referred to as PEG-Cer).

In some embodiments, lipids are cationic lipids (e.g., those described herein).

In some instances, modified forms of lipids may be used including forms modified with detectable labels such as fluorophores. In some instances, the lipid is a lipid analog that emits signal (e.g., a fluorescent signal). Examples include without limitation 1,1'-dioctadecyl-3,3,3',3'-tetramethylindotricarbocyanine iodide (DiR) and 1,1'-dioctadecyl-3,3,3',3'-tetramethylindodicarbocyanine (DiD).

In some embodiments, the lipids are biodegradable in order to allow release of encapsulated agent in vivo and/or in vitro. Biodegradable lipids include but are not limited to 1,2-dioleoyl-sn-glycero-3-phosphocholine (dioleoyl-phosphocholine, DOPC), anionic 1,2-di-(9Z-octadecenoyl)-sn-glycero-3-phospho-(1'-rac-glycerol) (dioleoyl-phosphoglycerol, DOPG), and 1,2-distearoyl-sn-glycero-3-phosphoethanolamine(distearoyl-phosphoethanolamine, DSPE). Non-lipid membrane components such as cholesterol may also be incorporated.

In some embodiments, at least one component of the lipid bilayer is functionalized (or reactive). As used herein, a functionalized component is a component that comprises a reactive group that can be used to crosslink adjacent bilayers of the multilamellar vesicle. The bilayer component may be modified to comprise the reactive group.

One or more of the lipids used in the synthesis of the vesicles may be functionalized lipids. As used herein, a functionalized lipid is a lipid having a reactive group that can be used to crosslink adjacent bilayers of the multilamellar vesicle. In some embodiments, the reactive group is one that will react with a crosslinker (or other moiety) to form crosslinks between such functionalized lipids (and thus between lipid bilayers in the vesicle). The reactive group may be located anywhere on the lipid that allows it to contact a crosslinker and be crosslinked to another lipid in an adjacent apposed bilayer. In some embodiments, it is in the head group of the lipid, including for example a phospholipid. An example of a reactive group is a maleimide group. Maleimide groups may be crosslinked to each other in the presence of dithiol crosslinkers such as but not limited to dithiolthrietol (DTT). An example of a functionalized lipid is 1,2-dioleoyl-sn-glycero-3-phosphoethanolamine-N-[4-(p-maleimidophenyl) butyramide, referred to herein as MPB. Another example of a functionalized lipid is 1,2-distearoyl-sn-glycero-3-phosphoethanolamine-N-[maleimide(polyethylene glycol)2000] (also referred to as maleimide-PEG 2k-PE). Another example of a functionalized lipid is dioleoyl-phosphatidylethanolamine 4-(N-maleimidomethyl)-cyclohexane-1-carboxylate (DOPE-mal).

It is to be understood that the disclosure contemplates the use of other functionalized lipids, other functionalized lipid bilayer components, other reactive groups, and other crosslinkers. In addition to the maleimide groups, other examples of reactive groups include but are not limited to other thiol reactive groups, amino groups such as primary and secondary amines, carboxyl groups, hydroxyl groups, aldehyde groups, alkyne groups, azide groups, carbonyls, haloacetyl (e.g., iodoacetyl) groups, imidoester groups, N-hydroxysuccinimide esters, sulfhydryl groups, pyridyl disulfide groups, and the like.

Functionalized and non-functionalized lipids are available from a number of commercial sources including Avanti Polar Lipids (Alabaster, Ala.).

It is to be understood that the disclosure contemplates various ways to link adjacent bilayers in the multilamellar vesicles to each other. In some instances, crosslinkers are used to effect linkage between adjacent bilayers. The disclosure however is not so limited.

The disclosure contemplates the delivery, including in some instances sustained delivery, of agents to regions, tissues or cells in vivo or in vitro using compositions of the disclosure. As used herein, an agent is any atom or molecule or compound that can be used to provide benefit to a subject (including without limitation prophylactic or therapeutic benefit) or that can be used for diagnosis and/or detection (for example, imaging) in vivo or that has use in in vitro applications.

Any agent may be delivered using the compositions and methods of the disclosure provided that it can be encapsulated into (including throughout) or otherwise carried on the stabilized MLVs provided herein. For example, the agent should be able to withstand the synthesis and optionally storage process for these vesicles. The vesicles may be synthesized and stored in, for example, a lyophilized form, preferably with a sucrose based excipient. The agents, if incorporated into the vesicles during synthesis, should be stable during such storage procedures and times.

The agent may be without limitation a protein, a polypeptide, a peptide (e.g. antigen), an antibody, a nucleic acid (e.g. DNA, mRNA, miRNA, lncRNA, etc.), a small molecule (e.g., chemical, whether organic or inorganic) drug, a virus-like particle, a steroid, a proteoglycan, a lipid, a carbohydrate, and analogs, derivatives, mixtures, fusions, combinations or conjugates thereof. The agent may be a prodrug that is metabolized and thus converted in vivo to its active (and/or stable) form. The agents may be naturally occurring or non-naturally occurring. Naturally occurring agents include those capable of being synthesized by the subjects to whom the vesicles are administered. Non-naturally occurring are those that do not exist in nature normally, whether produced by plant, animal, microbe or other living organism.

One class of agents is peptide-based agents such as (single or multi-chain) proteins and peptides. Examples include antibodies, single chain antibodies, antibody fragments, enzymes, co-factors, receptors, ligands, transcription factors and other regulatory factors, some antigens (as discussed below), cytokines, chemokines, and the like. These peptide-based agents may or may not be naturally occurring but they are capable of being synthesized within the subject, for example, through the use of genetically engineered cells.

Another class of agents that can be delivered using the vesicles of the disclosure includes those agents that are not peptide-based. Examples include chemical compounds that are non-naturally occurring, or chemical compounds that are not naturally synthesized by mammalian (and in particular human) cells.

A variety of agents that are currently used for therapeutic or diagnostic purposes can be delivered according to the disclosure and these include without limitation imaging agents, immunomodulatory agents such as immunostimulatory agents and immunoinhibitory agents, antigens, adjuvants, cytokines, chemokines, anti-cancer agents, anti-infective agents, nucleic acids, antibodies or fragments thereof, fusion proteins such as cytokine-antibody fusion proteins, Fc-fusion proteins, and the like.

Imaging Agents. As used herein, an imaging agent is an agent that emits signal directly or indirectly thereby allowing its detection in vivo. Imaging agents such as contrast agents and radioactive agents that can be detected using medical imaging techniques such as nuclear medicine scans and magnetic resonance imaging (MRI). Imaging agents for magnetic resonance imaging (MRI) include Gd(DOTA), iron oxide or gold nanoparticles; imaging agents for nuclear medicine include $^{201}$Tl, gamma-emitting radionuclide $^{99}$mTc; imaging agents for positron-emission tomography (PET) include positron-emitting isotopes, $^{18}$F-fluorodeoxyglucose ($^{18}$FDG), $^{18}$F-fluoride, copper-64, gadoamide, and radioisotopes of Pb(II) such as $^{203}$Pb, and $^{11}$In; imaging agents for in vivo fluorescence imaging such as fluorescent dyes or dye-conjugated nanoparticles. In other embodiments, the agent to be delivered is conjugated, or fused to, or mixed or combined with an imaging agent.

Immunostimulatory Agents. As used herein, an immunostimulatory agent is an agent that stimulates an immune response (including enhancing a pre-existing immune response) in a subject to whom it is administered, whether alone or in combination with another agent. Examples include antigens, adjuvants (e.g., TLR ligands such as imiquimod and resiquimod, imidazoquinolines, nucleic acids comprising an unmethylated CpG dinucleotide, monophosphoryl lipid A (MPLA) or other lipopolysaccharide derivatives, single-stranded or double-stranded RNA, flagellin, muramyl dipeptide), cytokines including interleukins (e.g., IL-2, IL-7, IL-15 (or superagonist/mutant forms of these cytokines), IL-12, anti-PD-1, ant-PD-L1, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like.

Antigens. The antigen may be without limitation a cancer antigen, a self or autoimmune antigen, a microbial antigen, an allergen, or an environmental antigen. The antigen may be peptide, lipid, or carbohydrate in nature, but it is not so limited.

Cancer Antigens. A cancer or tumor antigen is an antigen that is expressed preferentially by cancer cells (e.g., it is expressed at higher levels in cancer cells than on non-cancer cells) and in some instances it is expressed solely by cancer cells. The cancer antigen may be expressed within a cancer cell or on the surface of the cancer cell. The cancer antigen may be MART-1/Melan-A, gp100, adenosine deaminase-binding protein (ADAbp), FAP, cyclophilin b, colorectal associated antigen (CRC)-0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05). The cancer antigen may be selected from the group consisting of GAGE-1, GAGE-2, GAGE-3, GAGE-4, GAGE-5, GAGE-6, GAGE-7, GAGE-8, GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100$^{Pmel117}$, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, and c-erbB-2.

Microbial Antigens. Microbial antigens are antigens derived from microbial species such as without limitation bacterial, viral, fungal, parasitic and mycobacterial species. As such, microbial antigens include bacterial antigens, viral antigens, fungal antigens, parasitic antigens, and mycobacterial antigens. Examples of bacterial, viral, fungal, parasitic and mycobacterial species are provided herein. The microbial antigen may be part of a microbial species or it may be the entire microbe.

The present disclosure is not limited to the use of any one specific type of immunogen (e.g., inactivated pathogen, pathogen product, recombinant protein, etc.). Indeed, vaccines to a variety of pathogens are within the scope of the present disclosure. Accordingly, in some embodiments, the present disclosure provides vaccines to bacterial pathogens in vegetative or spore forms (e.g., including, but not limited to, *Bacillus cereus, Bacillus circulans* and *Bacillus megaterium, Bacillus anthracis, Clostridium perfringens, Vibrio cholerae, Streptococcus pyogenes, Streptococcus agalactiae, Streptococcus pneumonia, Staphylococcus aureus, Neisseria gonorrhea, Haemophilus influenzae, Escherichia coli, Salmonella typhimurium, Shigella dysenteriae, Proteus mirabilis, Pseudomonas aeruginosa, Yersinia enterocolitica,* and *Yersinia pseudotuberculosis*). In other embodiments, the present disclosure provides vaccines to viral pathogens (e.g., including, but not limited to, influenza A & B, herpes simplex virus I, herpes simplex virus II, respiratory synthetial virus, sendai, sindbis, vaccinia, parvovirus, human immunodeficiency virus, hepatitis B, virus hepatitis C virus, hepatitis A virus, cytomegalovirus, and human papilloma virus, picornavirus, hantavirus, junin virus, and ebola virus). In still further embodiments, the present disclosure provides vaccines to fungal pathogens, including, but not limited to, *Candida albicnas* and *parapsilosis, Aspergillus fumigatus* and *niger, Fusarium* spp, *Trychophyton* spp.

Bacteria for use in formulating the vaccines of the present disclosure can be obtained from commercial sources, including, but not limited to, American Type Culture Collection (ATCC). In some embodiments, bacteria are passed in animals prior to being mixed with liposomes or vesicles in order to enhance their pathogenicity for each specific animal host for 5-10 passages (Sinai et al., J. Infect. Dis., 141:193 (1980)). In some embodiments, the bacteria then are then isolated from the host animals, expanded in culture and stored at −80° C. Just before use, the bacteria are thawed and grown on an appropriate solid bacterial culture medium overnight. The next day, the bacteria are collected from the agar plate and suspended in a suitable liquid solution. The concentration of bacteria is adjusted so that the bacteria count is approximately $1.5 \times 10^8$ colony forming units per ml (CFU/ml) based on the McFarland standard for bactericidal testing (Hendrichson and Krenz, 1991).

Viruses for use in formulating the vaccines of the present disclosure can be obtained from commercial sources, including, but not limited, ATCC. In some embodiments, viruses are passed in the prospective animal model for 5-10 times to enhance pathogenicity for each specific animal (Ginsberg and Johnson, Infect. Immun., 13:1221 (1976)). In some embodiments, the virus is collected and propagated in tissue culture and then purified using density gradient concentration and ultracentrifugation (Garlinghouse et al., Lab Anim Sci., 37:437 (1987); and Mahy, Br. Med. Bull., 41:50 (1985)). The Plaque Forming Units (PFU) are calculated in the appropriate tissue culture cells.

Lethal dose and/or infectious dose for each pathogen can be calculated using any suitable method, including, but not limited to, by administering different doses of the pathogens to the animals by the infective route and identifying the doses which result in the expected result of either animal sickness or death based on previous publications (Fortier et al., Infect Immun., 59:2922 (1991); Jacoby, Exp Gerontol., 29:89 (1994); and Salit et al., Can J Microbiol., 30:1022 (1984)).

Allergens. An allergen is an agent that can induce an allergic or asthmatic response in a subject. Allergens include without limitation pollens, insect venoms, animal dander dust, fungal spores and drugs (e.g. penicillin). Examples of natural, animal and plant allergens include but are not limited to proteins specific to the following genera: *Canine* (*Canis familiaris*); *Dermatophagoides* (e.g. *Dermatophagoides farinae*); *Felis* (*Felis domesticus*); *Ambrosia* (*Ambrosia* artemiisfolia; *Lolium* (e.g. *Lolium perenne* or *Lolium multiflorum*); *Cryptomeria* (*Cryptomeria japonica*); *Alternaria* (*Alternaria alternata*); *Alder*; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens*, *Cupressus arizonica* and *Cupressus macrocarpa*); *Juniperus* (e.g. *Juniperus sabinoides*, *Juniperus virginiana*, *Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

Adjuvants. The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS1312, water-based nanoparticles combined with a soluble immunostimulant, Seppic)

Adjuvants may be TLR ligands. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

Immunoinhibitory Agents. As used herein, an immunoinhibitory agent is an agent that inhibits an immune response in a subject to whom it is administered, whether alone or in combination with another agent. Examples include steroids, retinoic acid, dexamethasone, cyclophosphamide, anti-CD3 antibody or antibody fragment, and other immunosuppressants.

Anti-Cancer Agents. As used herein, an anti-cancer agent is an agent that at least partially inhibits the development or progression of a cancer, including inhibiting in whole or in part symptoms associated with the cancer even if only for the short term. Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, *vinca* alkaloids, or epipodophyllotoxins.

Examples of anti-cancer agents include without limitation Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA), Esorubicin; Estramustine; Etanidazole; Etoposide; Etoprine; Fadrozole; Fazarabine; Fenretinide; Floxuridine; Fludarabine; 5-Fluorouracil; Fluorocitabine; Fosquidone; Fostriecin; Gefitinib (IRESSA), Gemcitabine; Hydroxyurea; Idarubicin; Ifosfamide; Ilmofosine; Imatinib mesylate (GLEEVAC); Interferon alpha-2a; Interferon alpha-2b; Interferon alpha-n1; Interferon alpha-n3; Interferon beta-I a; Interferon gamma-I b; Iproplatin; Irinotecan; Lanreotide; Lenalidomide (REVLIMID, REVIMID); Letrozole; Leuprolide; Liarozole; Lometerxol;

Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemeterxed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimeterxate; Triptorelin; Tubulozole; Uracil Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

The anti-cancer agent may be an enzyme inhibitor including without limitation tyrosine kinase inhibitor, a CDK inhibitor, a MAP kinase inhibitor, or an EGFR inhibitor. The tyrosine kinase inhibitor may be without limitation Genistein (4',5,7-trihydroxyisoflavone), Tyrphostin 25 (3,4,5-trihydroxyphenyl), methylene]-propanedinitrile, Herbimycin A, Daidzein (4',7-dihydroxyisoflavone), AG-126, trans-1-(3'-carboxy-4'-hydroxyphenyl)-2-(2",5"-dihydroxyphenyl)ethane, or HDBA (2-Hydroxy-5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 ($C_{23}H_{24}O_8$), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WH1-P97 (quinazoline derivative), LFM-A12 (leflunomide metabolite analog), ABX-EGF, lapatinib, canertinib, ZD-6474 (ZACTIMA), AEE788, and AG1458.

The anti-cancer agent may be a VEGF inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin.

The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), IOR-05, IOR-T6 (anti-CD1), IOR EGF/R3, celogovab (ONCOSCINT OV103), epratuzumab (LYMPHOCIDE), pemtumomab (THERAGYN), and Gliomab-H (indicated for brain cancer, melanoma).

Hematopoietic Differentiating Agents. The agent may be one that stimulates the differentiation of hematopoietic progenitor cells towards one or more lineages. Examples include without limitation IL-3, G-CSF, GM-CSF, M-CSF, thrombopoeitin, erythropoietin, WntSA, Wnt11A, and the like.

Hematopoietic Self-Renewing Agents. The agent may be one that stimulates the self-renewal of hematopoietic progenitor cells. Examples include without limitation kit ligand, GSK3-beta inhibitors, Wnt5A together with SLF, Notch1 activators, Lnk inhibitors, prostaglandin E2 (PGE2) and agents that stimulate the PGE2 pathway including PGE2, PGI2, Linoleic Acid, 13(s)-HODE, LY171883, Mead Acid, Eicosatrienoic Acid, Epoxyeicosatrienoic Acid, ONO-259, Cay1039, a PGE2 receptor agonist, of 16,16-dimethyl PGE2, 19(R)-hydroxy PGE2, 16,16-dimethyl PGE2 p-(p-acetamidobenzamido) phenyl ester, 11-deoxy-16,16-dimethyl PGE2,9-deoxy-9-methylene-16,16-dimethyl PGE2,9-deoxy-9-methylene PGE2, Butaprost, Sulprostone, PGE2 serinol amide, PGE2 methyl ester, 16-phenyl tetranor PGE2, 15(S)-15-methyl PGE2, 15(R)-15-methyl PGE2, BIO, 8-bromo-cAMP, Forskolin, Bapta-AM, Fendiline, Nicardipine, Nifedipine, Pimozide, Strophanthidin, Lanatoside, L-Arg, Sodium Nitroprusside, Sodium Vanadate, Bradykinin, Mebeverine, Flurandrenolide, Atenolol, Pindolol, Gaboxadol, Kynurenic Acid, Hydralazine, Thiabendazole, Bicuclline, Vesamicol, Peruvoside, Imipramine, Chlorpropamide, 1,5-Pentamethylenetetrazole, 4-Aminopyridine, Diazoxide, Benfotiamine, 12-Methoxydodecenoic acid, N-Formyl-Met-Leu-Phe, Gallamine, IAA 94, Chlorotrianisene, and derivatives thereof, and the like.

Anti-Infective Agents. The agent may be an anti-infective agent including without limitation an anti-bacterial agent, an anti-viral agent, an anti-parasitic agent, an anti-fungal agent, and an anti-mycobacterial agent.

Anti-bacterial agents may be without limitation β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, or quinolines.

Other anti-bacterials may be without limitation Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate;

Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfas alazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; or Zorbamycin. Anti-mycobacterial agents may be without limitation Myambutol (Ethambutol Hydrochloride), Dapsone (4,4'-diaminodiphenylsulfone), Paser Granules (aminosalicylic acid granules), Priftin (rifapentine), Pyrazinamide, Isoniazid, Rifadin (Rifampin), Rifadin IV, Rifamate (Rifampin and Isoniazid), Rifater (Rifampin, Isoniazid, and Pyrazinamide), Streptomycin Sulfate or Trecator-SC (Ethionamide).

Anti-viral agents may be without limitation amantidine and rimantadine, ribivarin, acyclovir, vidarabine, trifluorothymidine, ganciclovir, zidovudine, retinovir, and interferons. Anti-viral agents may be without limitation further include Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime or integrase inhibitors.

Anti-fungal agents may be without limitation imidazoles and triazoles, polyene macrolide antibiotics, griseofulvin, amphotericin B, and flucytosine. Antiparasites include heavy metals, antimalarial quinolines, folate antagonists, nitroimidazoles, benzimidazoles, avermectins, praxiquantel, ornithine decarboxylase inhibitors, phenols (e.g., bithionol, niclosamide); synthetic alkaloid (e.g., dehydroemetine); piperazines (e.g., diethylcarbamazine); acetanilide (e.g., diloxanide furonate); halogenated quinolines (e.g., iodoquinol (diiodohydroxyquin)); nitrofurans (e.g., nifurtimox); diamidines (e.g., pentamidine); tetrahydropyrimidine (e.g., pyrantel pamoate); or sulfated naphthylamine (e.g., suramin). Other anti-infective agents may be without limitation Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro); Aminacrine Hydrochloride; Benzethonium Chloride: Bithionolate Sodium; Bromchlorenone; Carbamide Peroxide; Cetalkonium Chloride; Cetylpyridinium Chloride: Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene: Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; or Troclosene Potassium.

Nucleic Acid Agents. Nucleic acids that can be delivered to a subject according to the disclosure include naturally or non-naturally occurring DNA (including cDNA, genomic DNA, nuclear DNA, mitochondrial DNA), RNA (including mRNA, rRNA, tRNA), oligonucleotides, a triple-helix forming molecule, immunostimulatory nucleic acids such as those described in U.S. Pat. No. 6,194,388 (the teachings of which relating to immunostimulatory CpG nucleic acids are incorporated herein by reference), small interfering RNA (siRNA) or microRNAs (miRNA) used to modulate gene expression, antisense oligonucleotides used to modulate gene expression, aptamers, ribozymes, a gene or gene fragment, a regulatory sequence, including analogs, derivatives, and combinations thereof. These nucleic acids may be administered neat or complexed to another entity, for example in order to facilitate their binding to and/or uptake by target tissues and/or cells.

Anti-Inflammatory Agents. Anti-inflammatory agents are agents that reduce or eliminate inflammation. They include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. One preferred anti-inflammatory agent is aspirin.

Other Agents. The agent may be without limitation adrenergic agent; adrenocortical steroid; adrenocortical suppressant; alcohol deterrent; aldosterone antagonist; ammonia detoxicant; amino acid; amylotropic lateral sclerosis agent; anabolic; analeptic; analgesic; androgen; anesthetic; anorectic; anorexic; anterior pituitary activator; anterior pituitary suppressant; anthelmintic; anti-acne agent; anti-adrenergic; anti-allergic; anti-amebic; anti-androgen; anti-anemic; antianginal; anti-anxiety; anti-arthritic; anti-asthmatic including β-adrenergic agonists, methylxanthines, mast cell stabilizing agents, anticholinergics, adrenocortical steroids such as glucocorticoids; anti-atherosclerotic; anticholelithic; anticholelithogenic; anticholinergic; anticoagulant; anticoccidal; anticonvulsant; antidepressant; antidiabetic; antidiarrheal; antidiuretic; antidote; antidyskinetic; anti-emetic; anti-epileptic; anti-estrogen; antifibrinolytic; antiglaucoma; antihemorrhagic; antihemorrheologic; antihistamine; antihyperlipidemic; antihyperlipoproteinemic; antihypertensive; antihypotensive; anti-infective; anti-inflammatory; antikeratinizing agent; antimigraine; antimitotic; antimycotic; antinauseant; antineutropenic; antiob sessional agent; antioxidant; antiparkinsonian; antiperistaltic; antpneumocystic; antiprostatic hypertrophy agent; antiprotozoal; antipruritic; antipsoriatic; antipsychotic; antirheumatic; antischistosomal; antiseborrheic; antisecretory; antispasmodic; antithrombotic; antitussive; anti-ulcerative; anti-urolithic; appetite suppressant; blood glucose regulator; bone resorption inhibitor; bronchodilator; carbonic anhydrase inhibitor; cardiac depressant; cardioprotectant; cardiotonic; cardiovascular agent; cerebral ischemia agent; choleretic; cholinergic; cholinergic agonist; cholinesterase deactivator; coccidiostat; cognition adjuvant; cognition enhancer; conjunctivitis agent; contrast agent; depressant; diagnostic aid; diuretic; dopaminergic agent; ectoparasiticide; emetic; enzyme inhibitor; estrogen; estrogen receptor agonist; fibrinolytic; fluorescent agent; free oxygen radical scavenger; gastric acid suppressant; gastrointestinal motility effector; geriatric agent; glucocorticoid; gonad-stimulating principle; hair growth stimulant; hemostatic; herbal active agent; histamine H2 receptor antagonists; hormone; hypocholesterolemic; hypoglycemic; hypolipidemic; hypotensive; HMGCoA reductase inhibitor; impotence therapy adjunct; inflammatory bowel disease agent; keratolytic; LHRH agonist; liver disorder agent; luteolysin; memory adjuvant; mental performance enhancer; mineral; mood regulator; mucolytic; mucosal protective agent; multiple sclerosis agent; mydriatic; nasal decongestant; neuroleptic; neuromuscular blocking agent; neuroprotective; NMDA antagonist; non-hormonal sterol derivative; nutrient; oxytocic; Paget's disease agent; plasminogen activator; platelet activating factor antagonist; platelet aggregation inhibitor; post-stroke and post-head trauma agents; progestin; prostaglandin; prostate growth inhibitor; prothyrotropin; psychotropic; radioactive agent; relaxant; rhinitis agent; scabicide; sclerosing agent; sedative; sedative-hypnotic; selective adenosine A1 antagonist; sequestering agents; serotonin antagonist; serotonin inhibitor; serotonin receptor antagonist; steroid; stimulant; suppressant; thyroid hormone; thyroid inhibitor; thyromimetic; tranquilizer; unstable angina agent; uricosuric; vasoconstrictor; vasodilator; vulnerary; wound healing agent; or xanthine oxidase inhibitor.

Embodiments of the present disclosure provide vaccine compositions comprising an antigen (e.g., peptide antigen) encapsulated in a liposome or vesicle described herein. In some embodiments, the vaccine is administered intranasally or using other methods.

In some embodiments, vaccine compositions comprise adjuvants. Adjuvants are described in general in Vaccine Design—the Subunit and Adjuvant Approach, edited by Powell and Newman, Plenum Press, New York, 1995, incorporated by reference herein in its entirety for all purposes. The present disclosure is not limited by the type of adjuvant utilized (e.g., for use in a composition (e.g., a pharmaceutical composition)). For example, in some embodiments, suitable adjuvants include an aluminium salt such as aluminium hydroxide gel (e.g., alum) or aluminium phosphate. In some embodiments, an adjuvant may be a salt of calcium, iron, or zinc, or it may be an insoluble suspension of acylated tyrosine, or acylated sugars, cationically or anionically derivatized polysaccharides, or polyphosphazenes.

In general, an immune response is generated to an antigen through the interaction of the antigen with the cells of the immune system. Immune responses may be broadly categorized into two categories: humoral and cell-mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an antigenic unit). Immune responses can be measured in many ways including activation, proliferation, or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

In some embodiments, a composition of the present disclosure may comprise sterile aqueous preparations. Acceptable vehicles and solvents include, but are not limited to, water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising a vaccine composition of the present disclosure can be used therapeutically (e.g., to enhance an immune response) or as a prophylactic (e.g., for immunization (e.g., to prevent signs or symptoms of disease)). A composition comprising a vaccine composition of the present disclosure can be administered to a subject via a number of different delivery routes and methods.

For example, the compositions of the present disclosure can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some embodiments, compositions of the present disclosure are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal, and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present disclosure may be administered dermally or transdermally using standard techniques (See, e.g., Remington: The Science arid Practice of Pharmacy, Mack Publishing Company, Easton, Pa., 19th edition, 1995). The present disclosure is not limited by the route of administration.

Although an understanding of the mechanism is not necessary to practice the present disclosure and the present disclosure is not limited to any particular mechanism of action, in some embodiments, mucosal vaccination is the route of administration as it has been shown that mucosal administration of antigens induces protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). In addition to inducing mucosal immune responses, mucosal vaccination also induces systemic immunity. In some embodiments, non-parenteral administration (e.g., muscosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising a vaccine composition of the present disclosure may be used to protect or treat a subject susceptible to, or suffering from, disease by means of administering a composition of the present disclosure via a mucosal route (e.g., an oral/alimentary or nasal route). Alternative mucosal routes include intravaginal and intra-rectal routes. In some embodiments of the present disclosure, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition is provided. Enteric formulations such as gastro resistant capsules for oral administration, suppositories for rectal or vaginal administration also form part of this disclosure. Compositions of the present disclosure may also be administered via the oral route. Under these circumstances, a composition comprising a vaccine composition may comprise a pharmaceutically acceptable excipient and/or include alkaline buffers or enteric capsules. Formulations for nasal delivery may include those with dextran or cyclodextran and saponin as an adjuvant.

Compositions of the present disclosure may also be administered via a vaginal route. In such cases, a composition comprising a vaccine composition may comprise pharmaceutically acceptable excipients and/or emulsifiers, polymers (e.g., CARBOPOL), and other known stabilizers of vaginal creams and suppositories. In some embodiments, compositions of the present disclosure are administered via a rectal route. In such cases, compositions may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response.

For example, in some embodiments, a composition comprising a vaccine composition is administered to a mucosal surface of a subject in either a priming or boosting vaccination regime. Alternatively, in some embodiments, the composition is administered systemically in either a priming or boosting vaccination regime. In some embodiments, a composition comprising a vaccine composition is administered to a subject in a priming vaccination regimen via mucosal administration and a boosting regimen via systemic administration. In some embodiments, a composition comprising a vaccine composition administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal, or intravenous administration. A composition comprising a vaccine composition may be used for both prophylactic and therapeutic purposes.

In some embodiments, compositions of the present disclosure are administered by pulmonary delivery. For example, a composition of the present disclosure can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colo.; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this disclosure is a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this disclosure are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers, and/or other agents useful in therapy. Also, the use of liposomes, microcapsules or microspheres, inclusion complexes, or other types of carriers is contemplated.

Thus, in some embodiments, a composition comprising a vaccine of the present disclosure may be used to protect and/or treat a subject susceptible to, or suffering from, a disease by means of administering the composition by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). The present disclosure may also be used to enhance a immunogenicity of antigens applied to the skin (transdermal or transcutaneous delivery, See, e.g., WO 98/20734; WO 98/28037, each of which are hereby incorporated by reference). Thus, in some embodiments, the present disclosure provides a delivery device for systemic administration, pre-filled with the vaccine composition of the present disclosure.

The present disclosure is not limited by the type of subject administered (e.g., in order to stimulate an immune response (e.g., in order to generate protective immunity (e.g., mucosal and/or systemic immunity))) a composition of the present disclosure. Indeed, a wide variety of subjects are contemplated to be benefited from administration of a composition of the present disclosure. In preferred embodiments, the subject is a human. In some embodiments, human subjects are of any age (e.g., adults, children, infants, etc.) that have been or are likely to become exposed to a microorganism (e.g., *E. coli*). In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present disclosure (e.g., to prevent the occurrence or spread of disease). For example, in some embodiments, compositions and methods of the present disclosure are utilized to vaccinate a group of people (e.g., a population of a region, city, state and/or country) for their own health (e.g., to prevent or treat disease). In some embodiments, the subjects are non-human mammals (e.g., pigs, cattle, goats, horses, sheep, or other livestock; or mice, rats, rabbits, dogs, cats, or other animal). In some embodiments, compositions and methods of the present disclosure are utilized in research settings (e.g., with research animals).

In some embodiments, a vaccine composition of the present disclosure is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the active ingredients in the concentrated composition. Concentrated compositions are contemplated to be useful in a setting in which large numbers of subjects may be administered a composition of the present disclosure (e.g., an immunization clinic, hospital, school, etc.). In some embodiments, a composition comprising a vaccine composition of the present disclosure (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition of the present disclosure (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eighth, ninth, tenth, and/or more than tenth administration. Although an understanding of the mechanism is not necessary to practice the present disclosure and the present disclosure is not limited to any particular mechanism of action, in some embodiments, reintroduction of an antigenic unit in a boost dose enables vigorous systemic immunity in a subject. The boost can be with the same formulation given for the primary immune response, or can be with a different formulation that contains the antigenic unit. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

It is contemplated that the compositions and methods of the present disclosure will find use in various settings, including research settings. For example, compositions and methods of the present disclosure also find use in studies of the immune system (e.g., characterization of adaptive immune responses (e.g., protective immune responses (e.g., mucosal or systemic immunity))). Uses of the compositions and methods provided by the present disclosure encompass human and non-human subjects and samples from those subjects, and also encompass research applications using these subjects. Compositions and methods of the present disclosure are also useful in studying and optimizing albumin variant, antigenic units, and other components and for screening for new components. Thus, it is not intended that the present disclosure be limited to any particular subject and/or application setting.

The present disclosure further provides kits comprising the vaccine compositions comprised herein. In some embodiments, the kit includes all of the components necessary, sufficient or useful for administering the vaccine. For example, in some embodiments, the kits comprise devices for administering the vaccine (e.g., needles or other injection devices), temperature control components (e.g., refrigeration or other cooling components), sanitation components (e.g., alcohol swabs for sanitizing the site of injection) and instructions for administering the vaccine.

EXPERIMENTAL

The following examples are provided in order to demonstrate and further illustrate certain preferred embodiments and aspects of the present disclosure and are not to be construed as limiting the scope thereof.

Example 1

Materials and Methods
Reagents

Lipids including 1,2-dioleoyl-3-trimethylammonium propane (DOTAP), 1,2-dioleoyl-sn-glycero-3-phosphoethanolamine (DOPE), nitrobenzoxadiazole (NBD)-labeled DOPE (DOPE-NBD), rhodamine (Rhod)-labeled DOPE (DOPE-Rhod), and MPLA were all purchased form Avanti Polar Lipids (Alabaster, Ala.). Sodium hyaluronate (HA) and 2 kDa PEG-SH were from Lifecore Biomedical (Chaska, Minn.) and Laysan Bio (Arab, Ala.), respectively. L-cysteine, N-(3-Dimethylaminopropyl)-N'-ethylcarbodiimide hydrochloride (EDC), N-hydroxysuccinimide (NETS), 5,5'-Dithiobis(2-nitrobenzoic acid) (DTNB) and chloramine T were obtained from Sigma-Aldrich (St. Louis, Mo.). Ovalbumin (OVA) and F1-V were obtained from Worthington (Lakewood, N.J.) and NIH BEI Resources (Manassas, Va.), respectively. RPMI 1640 media, fetal bovine serum (FBS), penicillin-streptomycin, β-mercaptoethanol and ACK lysis buffer were from Life Technologies (Grand Island, N.Y.). Granulocyte macrophage colony stimulating factor (GM-CSF) was the product of PeproTech (Rocky Hill, N.J.). Rat anti-mouse CD16/32, CD40-APC, and MHC Class II-FITC were from eBioscience (San Diego, Calif.). Rat anti-mouse CD86-biotin, CD8-APC, hamster anti-mouse CD11c-PE and streptavidin-Cy7 were from BD Bioscience (San Jose, Calif.). iTAg tetramer/PE-H-2 Kb OVA (SIINFEKL) was purchased from Beckman Coulter (Brea, Calif.). Zymax Rabbit anti-mouse IgG and HRP Rat anti-mouse $IgG_1$ were purchased from Invitrogen (Grand Island, N.Y.), and Goat anti-mouse $IgG_{2c}$ was from Southern Biotech (Birmingham, Ala.). 3.3',5.5'-tetramethylbenzidine (TMB) substrate solution was purchased from Thermo Scientific (Waltham, Mass.).

Thiolation of Hyaluronic Acid

Thiolated HA was synthesized by conjugation of HA with L-cysteine via EDC/NHS reaction. In specific, 200 mg HA was dissolved by 20 ml deionized water containing 200 mM EDC and NHS. The pH was then adjusted to 5 with 1 M HCl. The reaction mixture was stirred for 0.5 h, followed by addition of 400 mg L-cysteine and stirred at room temperature for another 4 h. The thiolated HA (HA-SH) was purified by dialysis (MWCO 10 kDa) against dilute HCl (pH 5), 0.9% NaCl in dilute HCl, and then dilute HCl again (1 day for each step). Finally, the dialyzed sample was lyophilized and stored at −80° C. The free thiol content of HA-SH was measured by Ellman's assay as previously reported (Schmitz T, Grabovac V, Palmberger T F, Hoffer M H, Bernkop-Schnurch A. Synthesis and characterization of a chitosan-N-acetyl cysteine conjugate. Int J Pharm. 2008; 347(1-2): 79-85). Briefly, 0.5 mg polymer was dissolved by 0.5 ml of 0.1 M sodium phosphate buffer (pH 8) containing 1 mM EDTA, followed by addition of 0.5 ml of 0.3 mg/ml DTNB solution. After incubation at room temperature for 2 h, absorbance of solution at 412 nm was measured to quantify the thiol content.

Preparation of Liposomes and Liposome-Polymer Hybrid NPs 0.5 mg DOTAP and 0.5 mg DOPE were dissolved in chloroform, followed by solvent evaporation to form lipid film. The dried lipid film was hydrated with 0.2 ml deionized water at room temperature for 1 h with intermittent vortex, followed by addition of varying amount of HA or HA-SH and incubation for 1 h for liposomal fusion. Next, 0.1 ml PEG-SH solution (5 mg/ml in 10 mM HEPES buffer, pH 7.4) was added and the pH was adjusted to 8 with 1 M sodium hydroxide. Then 50 µl of chloramine T solution (50 mM in HEPES buffer, pH 7.4) was added to induce thiol-mediated conjugation of PEG-SH onto HA-SH. After 1 h incubation at room temperature, the resulting particles were collected by centrifugation at 20,000×g for 10 min, washed with PBS, and finally resuspended in 0.2 ml PBS and stored at 4° C. till use. In some cases, the initial lipid film was prepared along with 2.9 µg of MPLA, and the hydrating solution containing 200 µg of OVA was used for the synthesis of OVA/MPLA-loaded DOTAP-HA NPs. Since MPLA with hydrophobic acyl chains has been previously shown to be efficiently incorporated into liposomes and lipid-based nanoparticles via self-assembly into lipid membranes (Moon J J, et al., Nat Mater. 2011; 10(3):243-51, Alving C R, et al., Expert Rev Vaccines. 2012; 11(6):733-44), 100% loading efficiency for MPLA in DOTAP-HA NPs was assumed. Encapsulation efficiency of OVA into NPs was determined to be 11±1.8%, as assessed by densiometry measurement of particle samples after running the samples through SDS-PAGE, followed by Coomassie staining.

Size and zeta potential of liposome-HA hybrid particle were measured by dynamic light scattering (Zetasizer Nano ZSP, Malvern, UK). Samples were diluted with deionized water or PBS and homogenized with brief sonication. PEG content in the final particle was determined by complexation of PEG with barium iodide as reported previously (Sims et al., Anal Biochem. 1980; 107(1):60-3; Gong W, et al., Talanta. 2007; 71(1):381-4). Briefly, 200 µl of 5% (w/v) barium chloride dissolved by 1 M hydrochloride acid and 100 µl of iodide solution containing 0.05 M iodine and 2% (w/v) potassium iodide was added to 800 µl of ×200 diluted particle suspension, followed by an incubation at room temperature for 15 min. Absorbance at 535 nm was measured for PEG quantification. The dry weight of particles after lyophilization was taken into account to report the PEG content in µmol/g of particles.

Liposomal Fusion Assay

The extent of polymer-induced liposomal fusion was assessed by the fluorescence resonance energy transfer (FRET) method (Hoekstra D. Biochemistry. 1982; 21(12): 2833-40; Osanai S, et al., Biomaterials. 2000; 21(9):867-76). Briefly, liposomes incorporating 5 mM DOPE-NBD (donor) or DOPE-Rhod (acceptor) were prepared separately, then mixed in 1:1 volume ratio, followed by addition of varying amounts of HA. After incubation at room temperature for 1 h, the samples were diluted 200 times and fluorescence intensity was measured by a microplate fluorometer (Synergy Neo, BioTek, USA) with excitation at 480 nm and emission filters set at 540 nm and 600 nm. FRET index was calculated as fluorescence intensity at 600 nm divided by that at 540 nm (Berney C, et al., Biophys J. 2003; 84(6):3992-4010).

Preparation of Bone Marrow Derived Cells (BMDCs)

BMDCs were prepared as described previously (Lutz M B, et al., J Immunol Methods. 1999; 223(1):77-92). In brief, femur and tibia were harvested from C57BL/6 mice, and cells were collected by flushing bone marrow with a syringe and passing the cell suspension through a cell strainer (mesh size=40 µm). After centrifugation, cells were seeded into non-tissue culture treated petri-dish at a density of $2 \times 10^6$ cells/ml in DC culture media (RPMI 1640 supplemented with 10% FBS, 1% penicillin-streptomycin, 50 µM β-mercaptoethanol, and 20 ng/ml GM-CSF), cultured at 37° C. with 5% $CO_2$. Culture media were refreshed on days 3, 6 and 8, and BMDCs were used on days 10-12.

Activation of BMDCs

BMDCs were seeded at a density of $8 \times 10^5$ cells/ml into 24-well plates and cultured overnight. Cells were incubated with culture media, liposomes or liposome-polymer hybrid NPs encapsulating 5 µg/ml of OVA, with or without 0.58 µg/ml of MPLA at 37° C. for 2 h, followed by washing with PBS and overnight culture. BMDCs were harvested, incubated with CD16/32 Fc at room temperature for 10 min, and then stained with fluorescent probe-labeled antibodies against CD40, MHC II, CD11c, and CD86 at room temperature for 30 min. Finally, cells were washed and resuspended in 2 µg/ml DAPI solution and analyzed by flow cytometry (Cyan 5, Beckman Coulter, USA).

Viability of BMDCs

BMDC viability following different treatments was measured by CCK-8 kit (Mosmann T. Rapid colorimetric assay for cellular growth and survival: application to proliferation and cytotoxicity assays. J Immunol Methods. 1983; 65(1-2):55-63). In brief, BMDCs were seeded into 96-well plates (40,000 cells/well) and cultured overnight. Cells were then incubated with liposomes or liposome-polymer hybrid NPs encapsulating OVA, with or without MPLA, with various lipid concentrations. Following 2 h incubation at 37° C., cells were washed by PBS and cultured overnight. Finally, cells were incubated with CCK-8 reagent for 2 h at 37° C. and OD450 was measured with a microplate reader.

In Vivo Immunization Studies

All in-vivo experiments were performed under approval from Institutional Animal Care and Use Committee (IACUC) at University of Michigan. Female, 6-week old C57BL/6 mice (The Jackson Laboratory, USA) were randomly divided into 3 groups (n=3–7) and administered with PBS, OVA plus MPLA solution or hybrid NPs co-encapsulating OVA and MPLA via intranasal route of immunization. Each dose contained 50 µg of OVA and 0.58 µg of MPLA. A booster dose was given on day 28 after the prime vaccination. Sera samples were collected on days 21 and 49 and stored at −80° C. until further analysis by ELISA. For studies with F1-V, mice (n=4) were intranasally immunized with F1-V plus MPLA solution or hybrid NPs co-encapsulating F1-V and MPLA. The doses for prime vaccination on day 0 and 1$^{st}$ booster vaccination on day 28 were 1 µg F1-V and 0.58 µg MPLA per mouse, while the 2' booster dose given on day 56 was increased to 5 µg F1-V and 2.9 µg of MPLA per mouse. Sera samples were collected on days 0, 7, 21, 35, 49, 63 and 77 post the prime dose.

Enzyme Linked Immunosorbent Assay (ELISA)

ELISA was used to determine sera anti-OVA or anti-F1-V antibody titers post immunization. Micro titer plate was coated with OVA (1 µg/well) or F1-V (200 ng/well) dissolved in carbonate-bicarbonate buffer (pH 9.6) at 4° C. overnight. Wells were washed and blocked by 1% BSA for 2.0 h, followed by incubation with serially diluted sera at room temperature for 1 h. HRP-conjugated anti-IgG, IgG$_1$ or IgG$_{2c}$ was added and incubated with samples for another hour, followed by colorization with TMB substrate solution for 5 min. The reaction was stopped by 2 M H$_2$SO$_4$, and absorbance at 450 nm was measured by a microplate reader.

Analysis of OVA-Specific CD8$^+$ T Cells Among Peripheral Blood Mononuclear Cells (PBMCs)

C57BL/6 mice (n=3) were intranasally immunized with PBS, OVA plus MPLA solution, or hybrid NPs loaded with OVA and MPLA. The dose was 50 µg of OVA and 0.58 µg of MPLA. Blood samples were collected 7 days after vaccination for tetramer staining assay. In brief, samples were lysed with ACK lysis buffer, followed by centrifugation to collect pellets, which were then blocked by CD16/32 Fc blocking antibody and incubated with PE labeled SIINFEKL tetramer for 30 min. Samples were then incubated with anti-CD8-APC for 20 min on ice. Cells were washed and resuspended in 2 µg/ml DAPI solution for analysis by flow cytometry.

Statistical Analysis

Data were analyzed by one- or two-way analysis of variance (ANOVA), followed by Bonferroni's test for comparison of multiple groups with Prism 5.0 (GraphPad Software). P values less than 0.05 were considered statistically significant, and marked with one asterisk. P values less than 0.001 were marked with three asterisks, while p values less than 0.0001 were marked with four asterisks. All values are reported as means±SEM with at least triplicate data points.

Results

Lipid-Polymer Hybrid NPs Formed by Polymer-Mediated Liposomal Fusion

Liposome-polymer hybrid NPs were synthesized by utilizing ionic complexation of positively charged liposomes and negatively charged hyaluronic acid (HA). As shown in FIG. 1a, the initial liposomes hydrated from lipid films composed of DOTAP and DOPE (henceforth referred to as DOTAP liposomes) had the particle size of 91±0.41 nm. As an increasing amount of HA was added to the unilamellar liposomes, their size gradually increased, reaching 160±1.4 nm with 150 µg HA added per 1 mg of liposome suspension. Addition of more than 300 µg of HA caused non-homogeneous aggregation shown by abrupt increases in particle sizes (FIG. 1a) and PDI values (FIG. 1b). Similarly, zeta potential of the lipid-polymer hybrid particles maintained values ranging from 47-55 mV with 0-150 µg HA added per 1 mg of liposome suspension (FIG. 1c). Addition of 300 µg of HA sharply decreased the surface charge of lipid-polymer hybrid particles, with their zeta potential readings reaching negative values with HA≥1000 µg.

Figure 2:
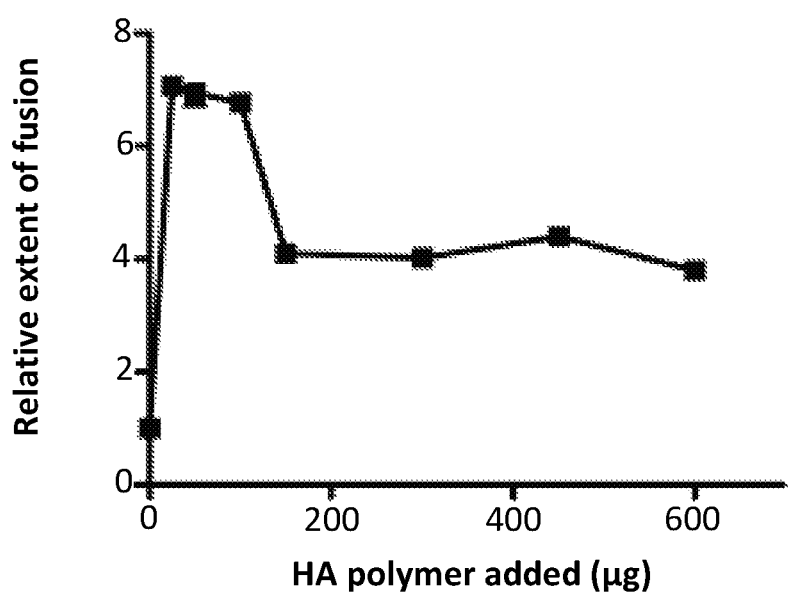
FIG. 2 shows polymer-induced fusion of liposomes.

HA-induced liposomal fusion was further assessed by measuring lipid mixing using the FRET assay, in which the efficiency of resonance energy transfer was measured between fluorescent NBD-(donor) and rhodamine-(acceptor) lipids initially on separate DOTAP liposomes and intermixed after addition of varying amount of HA. As shown in FIG. 2, addition of even 25 µg HA into liposomal suspension efficiently induced fusion of liposomes. The extent of fusion was decreased when more than 150 µg of HA was added to the batch of liposomes, suggesting that excess HA with anionic charge may coat the external surfaces of cationic DOTAP liposomes and reduce the extent of liposomal fusion. Based on the ability to induce liposomal fusion and formation of lipid-polymer hybrid NPs with homogeneous particle size, we chose to synthesize the hybrid NPs with 100 µg of HA for the subsequent studies.

In addition, to coat the external surfaces of liposome-HA hybrid particles with hydrophilic PEG shell, free sulfhydryl groups were introduced to HA by EDC-mediated reaction between carboxylic groups in HA and amine group in L-cysteine. Ellman's assay indicated that thiolated HA contained 310±1.8 µmol/g of free sulfhydryl groups. Analyses of DOTAP liposomes fused with varying amount of thiolated HA showed similar trends in terms of particle size, PDI, and zeta potential values as in FIG. 1, indicating that introduction of sulfhydryl groups in HA did not significantly alter the ability of biopolymer to induce liposomal fusion and formation of NPs. DOTAP liposomes fused with 100 µg of thiolated HA and PEGylated by incubation with 2 kDa MW thiol-PEG are referred to as DOTAP-HA NPs, and their characterization is summarized in Table 1. The PEG content was measured in DOTAP-HA NPs by assessing complexation of PEG with barium iodide as reported previously (Sims et al., supra; Gong e al., supra), and the results indicated that ~24% of thiol-PEG was conjugated on the surfaces of DOTAP-HA NPs with PEG concentration of 47±4.0 µmol per gram of particles. Similar assays were carried out with DOTAP-HA NPs loaded with OVA, and the results showed that incorporation of OVA led to modest increases in particle size and PDI, whereas PEGylation efficiency and PEG content remained similar.

TABLE 1

Characterization of DOTAP-HA NPs. Results are reported as mean ± SEM (n = 3).

| | Size (nm) | PDI | Zeta potential (mV) | PEGylation efficiency (%) | PEG content (µmol/g particle) |
|---|---|---|---|---|---|
| Blank DOTAP-HA NPs | 190 ± 1.3 | 0.18 ± 0.0017 | −17 ± 0.067 | 24 ± 4.5 | 47 ± 4.0 |
| OVA-loaded DOTAP-HA NPs | 250 ± 12 | 0.25 ± 0.0048 | −15 ± 0.93 | 22 ± 0.85 | 51 ± 13 |

Maturation of and Toxicity to BMDCs by DOTAP-HA NPs In Vitro

Figure 3:
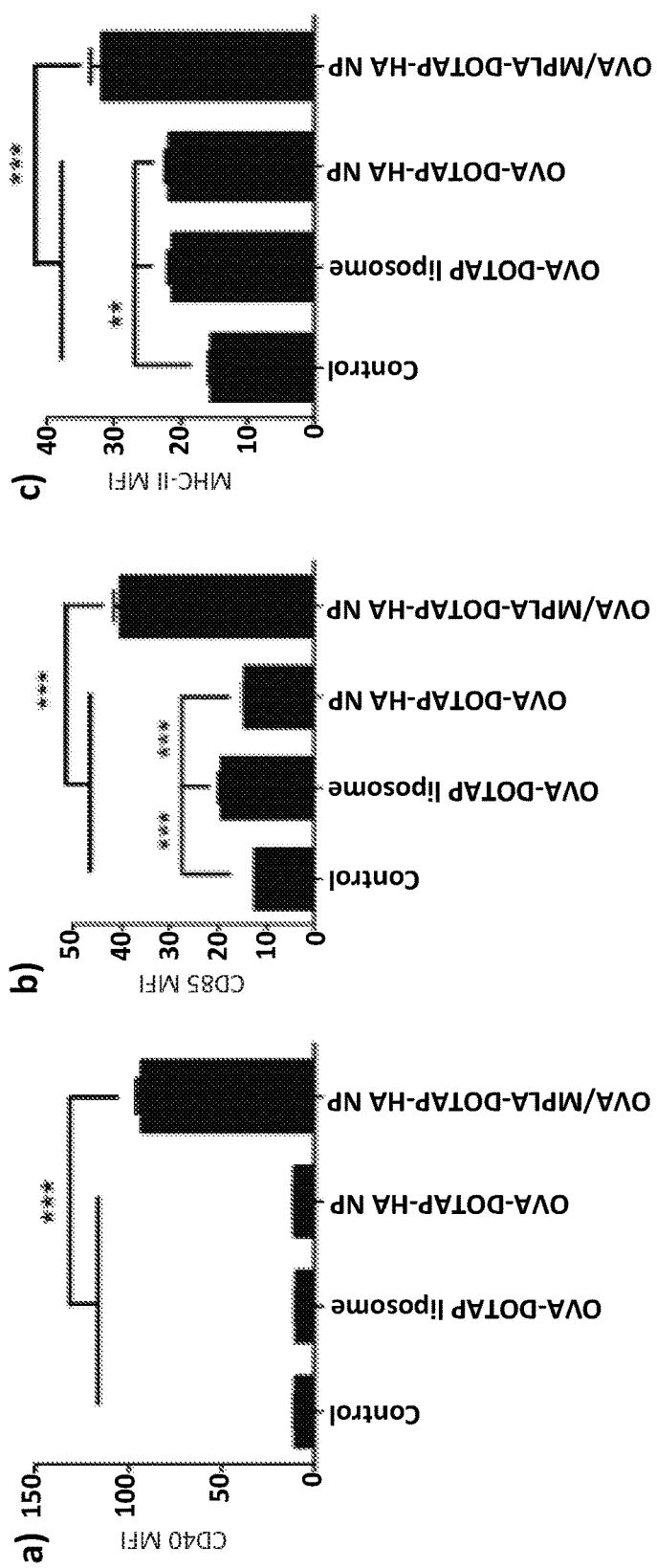
FIG. 3 shows maturation of BMDCs induced by different particles.

Maturation of dendritic cells (DCs) involves the up-regulation of a series of cell surface markers (Banchereau J, et al., Nat Rev Immunol. 2005; 5(4):296-306), including co-stimulatory molecules CD40 and CD80, and MHC-II responsible for antigen presentation to CD4+ T cells. DC activation was investigated by co-culturing BMDCs with different particles (FIG. 3). BMDCs exhibited minor increase in the expression levels of CD86 and MHC-II after treatment with OVA-DOTAP liposomes, while treatment with OVA-DOTAP-HA NPs led to slight increase in the expression levels of MHC-II, indicating low immunogenicity of particles without any danger signals. To promote DC maturation, we incorporated MPLA, a FDA-approved TLR4 agonist, into DOTAP-HA NPs by adding MPLA into the initial lipid film. Compared with OVA-DOTAP-HA NPs, DOTAP-HA NPs co-loaded with OVA and MPLA significantly up-regulated CD40 (FIG. 3a), CD86 (FIG. 3b) and MHC-II (FIG. 3c) on DCs, indicating superior immunogenicity of DOTAP-HA NPs carrying MPLA as a danger signal.

Figure 4:
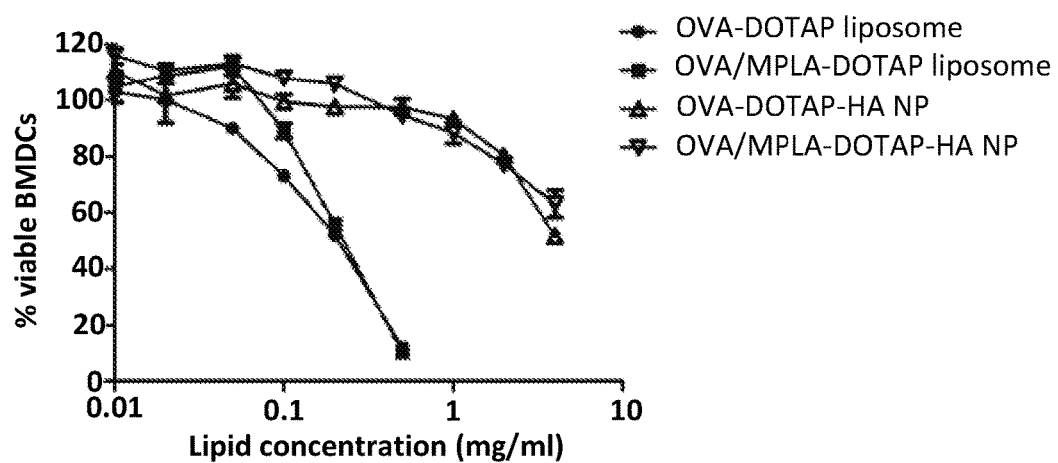
FIG. 4 shows cytotoxicity of DOTAP liposomes and DOTAP-HA NPs.

One of the major concerns of using DOTAP as a delivery vehicle is its reported cytotoxicity (Banchereau J, et al., supra). To compare cytotoxicity of DOTAP liposomes and DOTAP-HA NPs, BMDCs were pulsed with various concentrations of OVA-DOTAP liposomes or OVA-DOTAP-HA NPs with or without MPLA. After 2 hours of treatment, BMDCs were washed in PBS and cultured overnight. Measurement of cell viability showed that OVA-DOTAP liposome formulations with or without MPLA induced significant cytotoxicity in BMDCs with 50% of cell death observed at $LC_{50}$ value of ~0.2 mg/ml (FIG. 4). In contrast, BMDCs were able to tolerate at least 20-fold higher concentration of lipids in OVA-DOTAP-HA NPs ($LC_{50}>4$ mg/ml). These results showed that fusion of DOTAP liposomes with HA biopolymer significantly enhanced their biocompatibility; this may be attributed to masking of cationic DOTAP lipids with HA and/or PEG layer on DOTAP-HA NPs. Overall, liposome-HA hybrid NPs potently activated DCs with significantly reduced cytotoxicity, compared with DOTAP liposomes.

Adaptive Immune Responses Induced by Vaccine DOTAP-HA NPs

Figure 5:
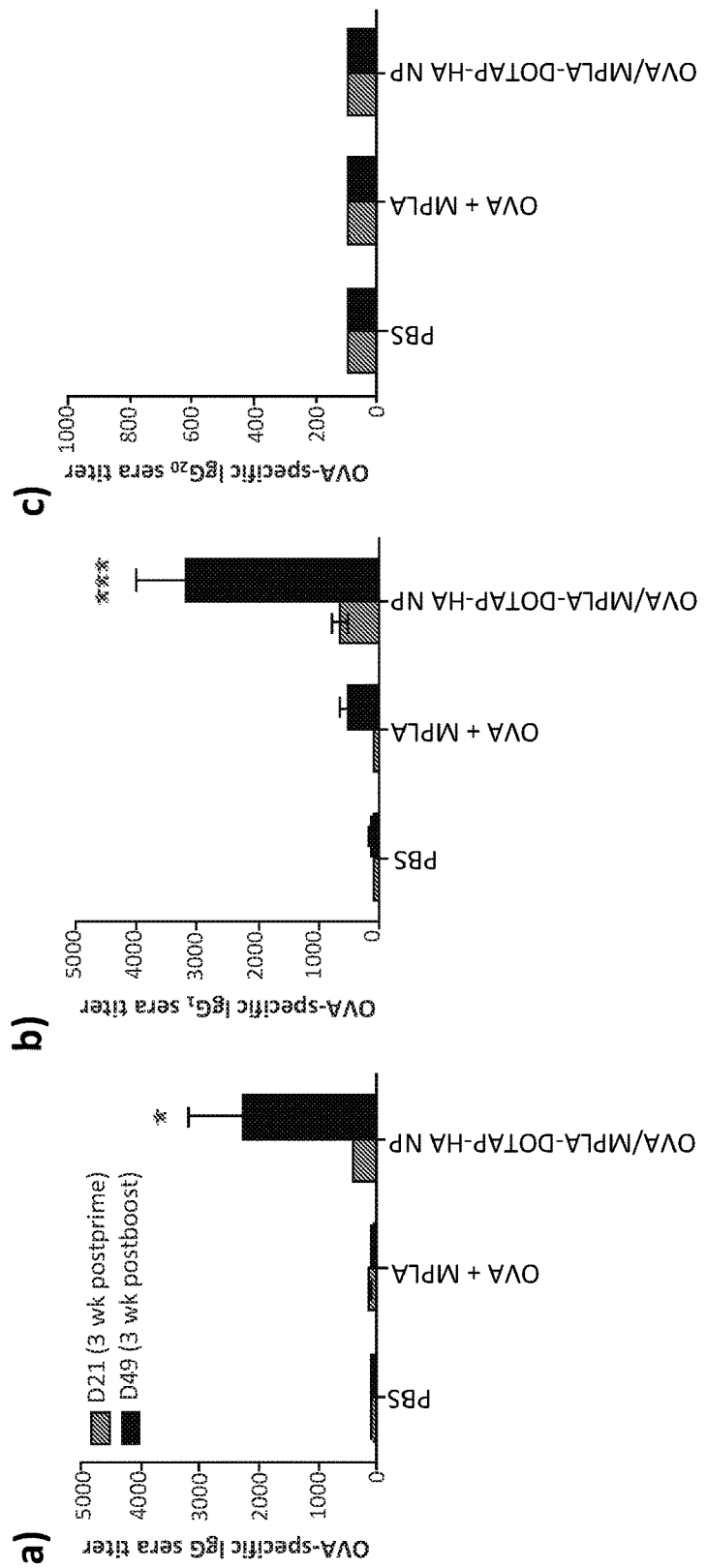
FIG. 5 shows OVA-specific humoral immune responses. Sera samples were collected on days 21 and 49 for analysis of OVA-specific total IgG (a), IgG1 (b) and IgG26*9c (c) titers by ELISA. *p<0.05 and ***p<0.001 in comparison to PBS and solution groups on day 49 as analyzed by two-way ANOVA, followed by Bonferroni's test for comparison of multiple groups.
Figure 6:
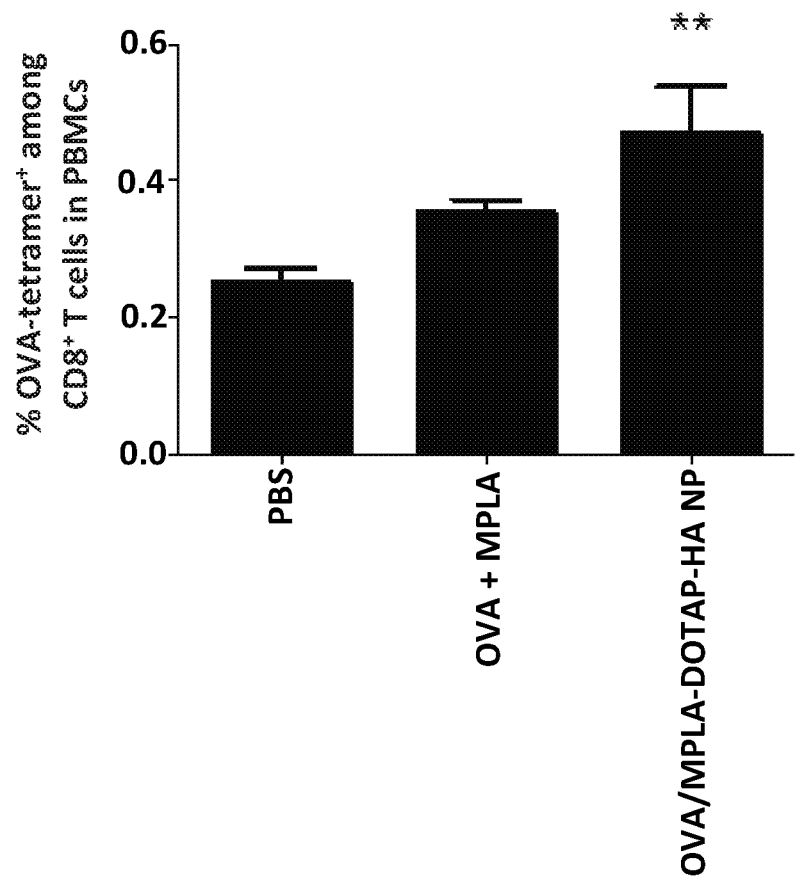
FIG. 6 shows OVA-specific cellular immune responses.

Next, the induction of humoral and cellular immune responses after intranasal delivery of OVA and MPLA in either soluble form or DOTAP-HA NPs was investigated. C57BL/6 mice were immunized with 50 μg of OVA and 0.58 μg of MPLA either in solution or DOTAP-HA NPs via intranasal administration on days 0 and 28. Immune sera were collected on days 21 and 49, 3 weeks post prime and boost, respectively, and analyzed for OVA-specific IgG responses with ELISA. Elicitation of significant level of OVA-specific IgG was detected from DOTAP-HA NPs group, but not from soluble vaccines (FIG. 5a). Among IgG subtypes, a robust level of OVA-specific $IgG_1$ response was observed (FIG. 5b); however, $IgG_{2c}$ responses were not detected (FIG. 5c), indicating strong skewing of Th2 over Th1 humoral immune responses with the OVA antigen (Matsuo K, et al., J Control Release. 2012; 161(1):10-7; Saade F, et al., Vaccine. 2013; 31(15):1999-2007). Elicitation of OVA-specific cellular immune responses was examined by assessing the frequency of OVA-specific CD8+ T cells among peripheral blood mononuclear cells (PBMCs) on day 7 after vaccination (FIG. 6). Compared with the PBS group, vaccination with DOTAP-HA NPs significantly increased the frequency of OVA-specific CD8+ T cells among PBMCs as measured with fluorophore-conjugated tetramer with $OVA_{257-264}$ (SIINFEKL) in the context of $H-2K^b$. There was also a trend for enhanced OVA-specific CD8+ T cell responses in the DOTAP-HA NP group, compared with the soluble vaccine group. In summary, intranasal vaccination with DOTAP-HA NPs enhanced both B- and T-cell immune responses, compared with the equivalent dose of soluble vaccines.

Figure 7:
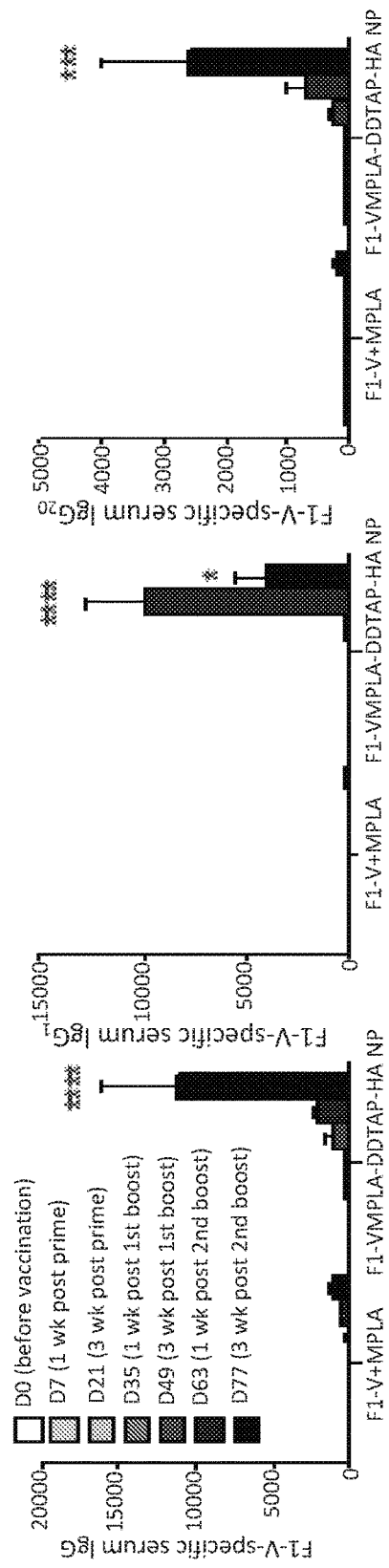
FIG. 7 shows F1-V-specific humoral immune responses. Sera were collected on days 0, 7, 21, 35, 49, 63 and 77 and analyzed for F1-V-specific total IgG (a), IgG1 (b) and IgG2c (c) titers by ELISA. *$p<0.05$, *$p<0.001$, and **$p<0.0001$ in comparison to the soluble F1-V plus MPLA group of the same time point as analyzed by two-way ANOVA, followed by Bonferroni's test for comparison of multiple groups. Results are reported as mean±SEM (n=4).

Elicitation of Humoral Immune Responses Against F1-V Post Intranasal Vaccination with DOTAP-HA NPs DOTAP-HA NPs were also used to deliver F1-V via intranasal route of vaccination. C57BL/6 mice were immunized with F1-V and MPLA either in soluble form or DOTAP-HA NPs, and the immune sera were analyzed for F1-V specific antibody titers. The prime and first boost doses given on day 0 and 28 contained 1 μg F1-V and 0.58 μg MPLA per mouse. Although there was a detectable increase in anti-F1-V IgG titers after the first boost immunization, due to low overall IgG responses, the second booster dose was increased to 5 μg F1-V and 2.9 μg MPLA per mouse to ensure sero-conversion and to more clearly distinguish the potency of soluble vs. particulate vaccine formulations. After the second booster doses, the hybrid NP delivery system elicited substantially higher F1-V-specific total IgG titers, compared with soluble F1-V vaccines (11-fold increase on day 77, p<0.0001, FIG. 7a). Analyses of F1-V-specific $IgG_1$ (FIG. 7b) and $IgG_{2c}$ (FIG. 7c) responses also revealed similar trend with 23-fold (p<0.05) and 15-fold increases (p<0.001) in sera titers on day 77, compared with immune sera from mice immunized with soluble F1-V vaccines. Notably, $IgG_1$ responses induced by DOTAP-HA NPs reached their peak on day 63 (1 week post the second boost) and started to decrease by day 77. On the other hand, $IgG_{2c}$ responses continued to increase after the second boost and reached substantially enhanced sera titer by day 77, contributing to the overall anti-F1-V total IgG titer. Thus, unlike the case with the OVA antigen (FIG. 5), F1-V delivered by DOTAP-HA NPs exhibited Th1/Th2-balanced humoral immune responses, indicating that the identity of subunit antigen formulated into these vaccines NPs has a direct impact on the Th1/Th2 humoral immune responses.

Liposome-polymer hybrid NPs was constructed and tested as a nasal vaccine delivery system. Cationic DOTAP liposomes were fused by HA and PEGylated for colloidal stability. When protein antigens and a molecular adjuvant were incorporated into the NPs, the particulate vaccine more efficiently promoted DC maturation and stimulated stronger humoral and cellular immune responses, compared with soluble vaccine formulations. Intranasal vaccination with NPs co-loaded with F1-V antigen and MPLA led to significantly stronger serum IgG responses, characterized by Th1/Th2-balanced humoral immune responses, indicating the potential of the hybrid DOTAP-HA NP system for prophylactic vaccination against infectious pathogens.

Example 2

Figure 8:
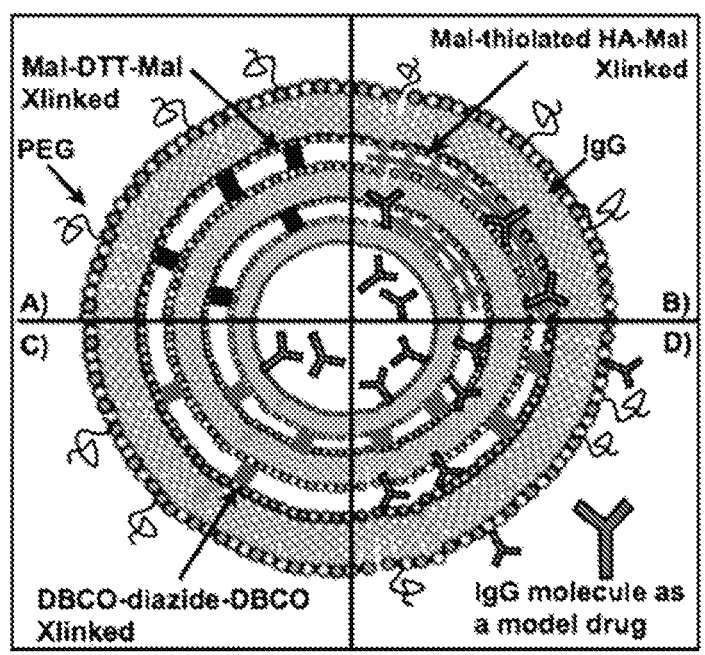
FIG. 8 shows exemplary multilamellar vesicular platforms (MVPs). (a) ICMVs formed by DTT-crosslinked maleimide lipids. (b) ICMVs with HA replacing DTT as a crosslinked. (c) MVPs formed by diazide crosslinked dibenzyocylooctyne (DBCO) lipids, loaded with IgG molecules. (d) IgG modified with free sulfhydryl moieties membrane-anchored throughout multiple lipid layers within MVPs via the use of maleimide-DOBAQ lipids.
Figure 9:
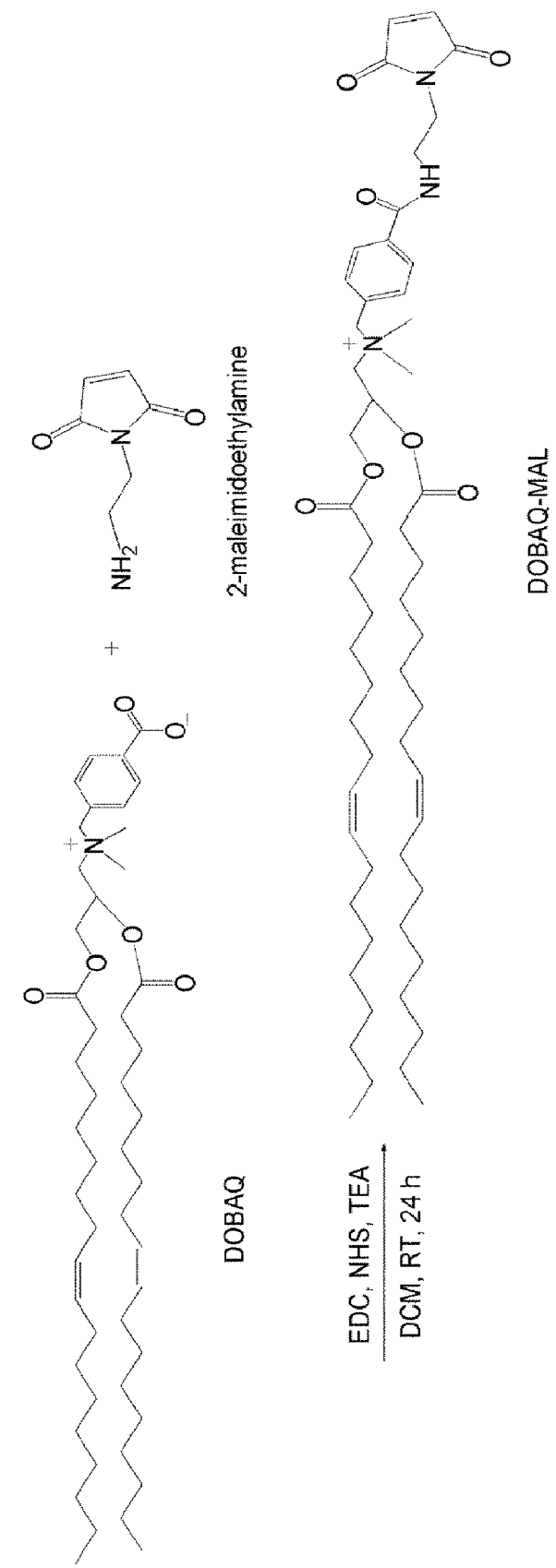
FIG. 9 shows synthesis scheme of DOBAQ-MAL.
Figure 10:
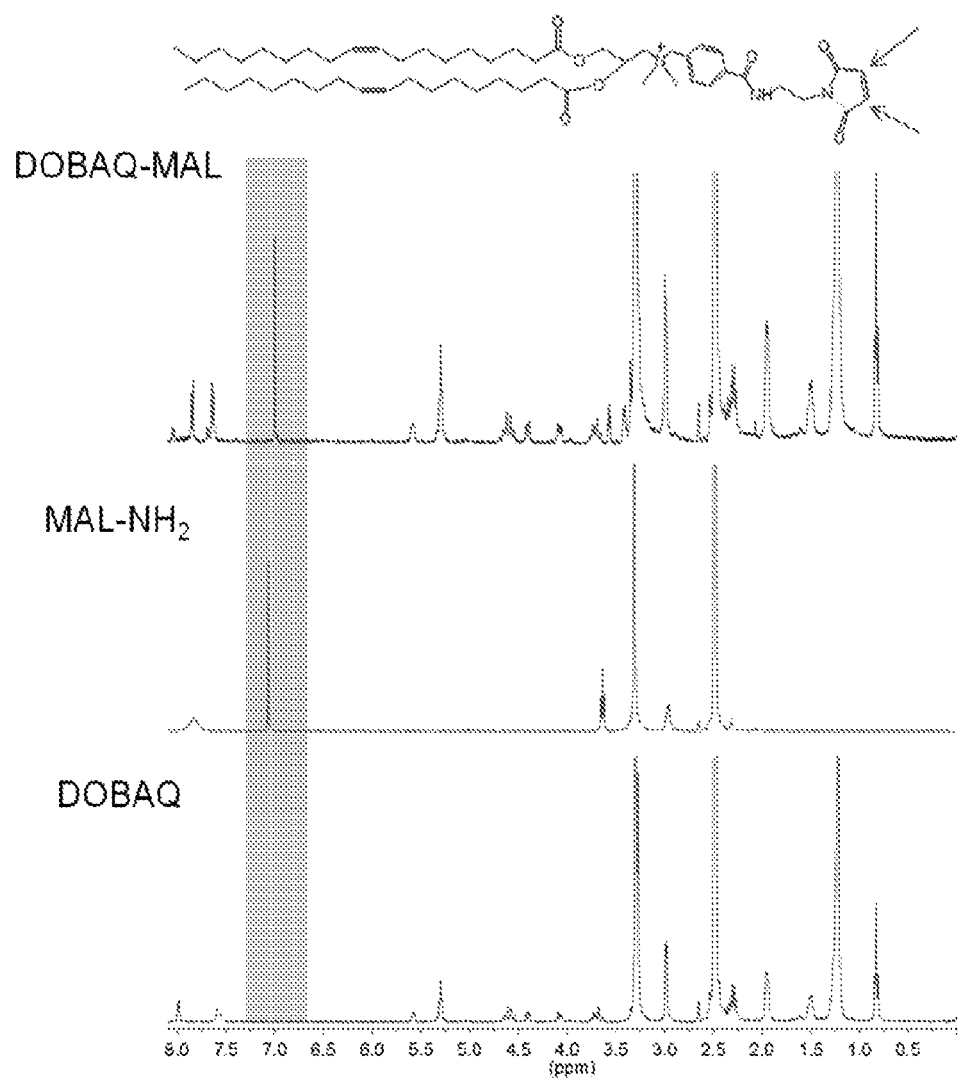
FIG. 10 shows $^1$H-NMR graphs of reactants DOBAQ and 2-maleimidoethylamine, and the product.
Figure 11:
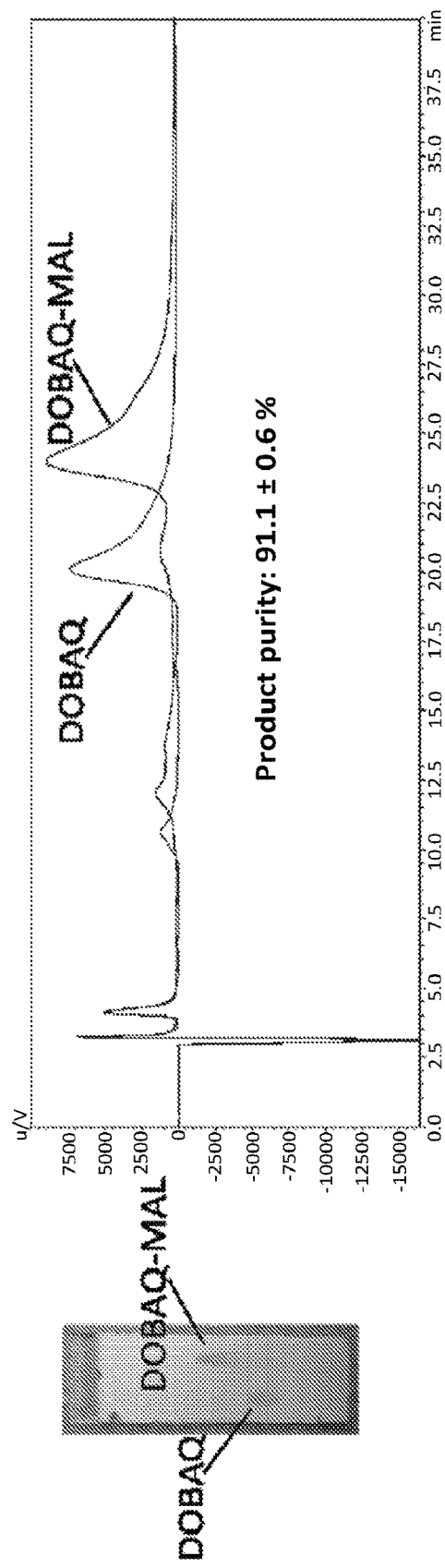
FIG. 11 shows identification of DOBAQ-MAL by TLC and HPLC.
Figure 12:
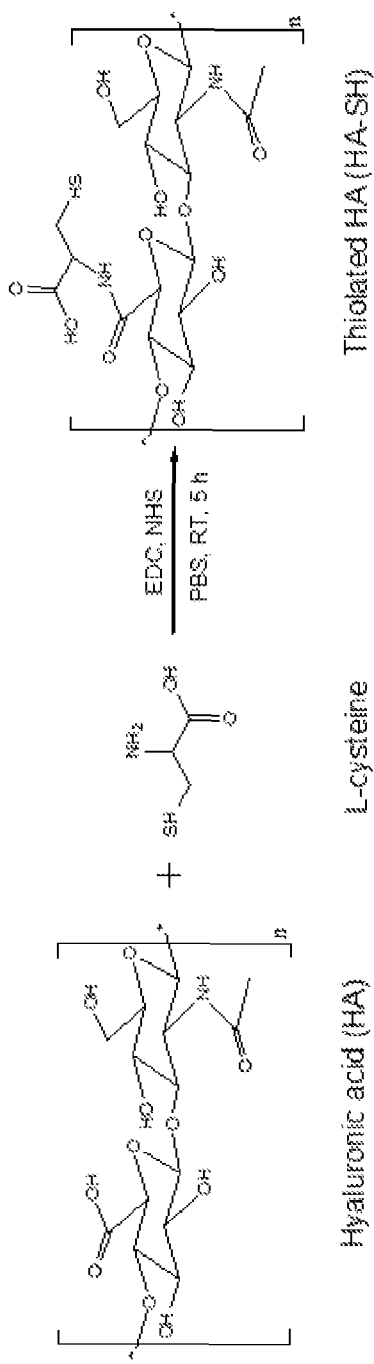
FIG. 12 shows synthesis scheme of HA-SH.
Figure 13:
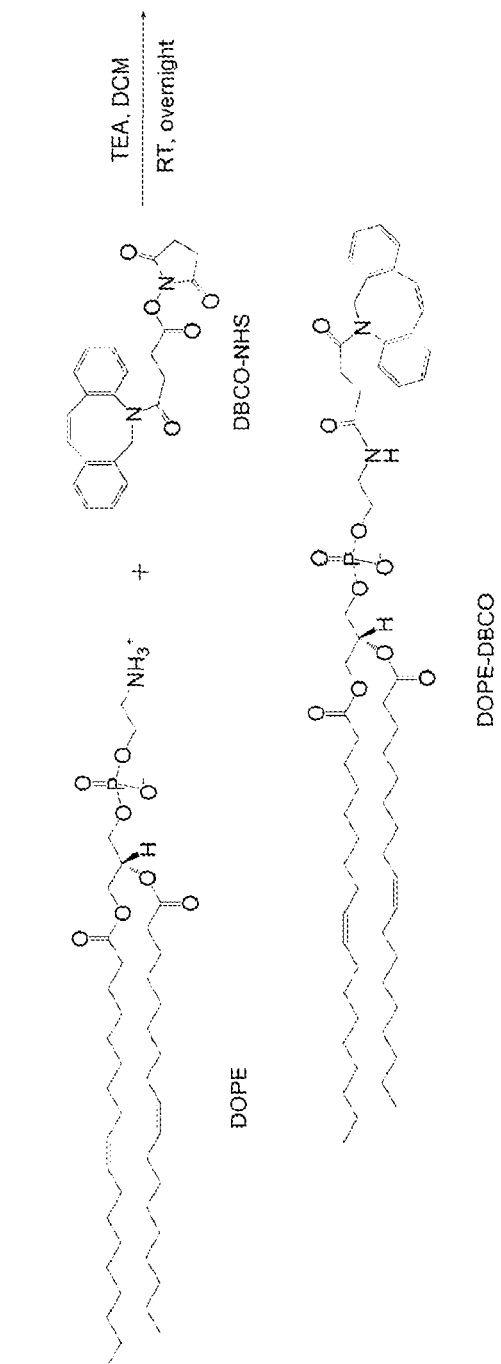
FIG. 13 shows synthesis scheme of DOPE-DBCO.

Previously, a lipid-based nanoparticle system, called interbilayer-crosslinked multilamellar vesicles (ICMVs) that allow efficient encapsulation and sustained release of proteins for 30 days were described (Moon et al., Nat Mater 10, 243-251, 2011). Their potency as macromolecule delivery vehicles was demonstrated by delivering protein antigens in vivo, which significantly enhanced cellular and humoral immune responses compared to conventional vaccine systems. The "standard" ICMVs are crosslinked by DTT (FIG. 8A), which is a strong reducing agent that can reduce disulfide bonds in protein/peptide antigens, thus potentially disrupting 3D structure of encapsulated macromolecules. Another major limitations of ICMVs is that they are synthesized by linking phospholipids using bifunctional cross-linkers (resulting in only two phospholipid molecules cross-linked per one DTT molecule as shown in FIG. 8A), which were identified as the major limiting factor in MVP stability. Provided herein are approaches to (1) avoid the use of reducing agent for synthesis of MVPs and (2) increase serum stability, thus achieving superior sustained release of cargo materials.

Three complementary approaches of material modification in order to synthesize MVPs that can withstand high serum content in physiological condition while encapsulating macromolecules (e.g., IgG molecules) without disruption of disulfide bonds are described.

Biopolymers as a Fusogenic and Multivalent Crosslinking Agent to Form MVPs.

Biopolymers modified with thiol groups are utilized as an inducer of fusion and crosslinking reagent between lipid vesicles decorated with maleimide-functionalized lipids. For an example, cationic liposomes composed of DOTAP:DOPC in 1:1 molar ratio were synthesized, and anionic hyaluronic acid polymer was added to the liposome suspension to initiate ionic complexation and fusion between lipid vesicles. This work has demonstrated that attractive charge interactions between lipid vesicles and biopolymers can be exploited to form serum-stable nanoparticles. Maleimide-functionalized cationic lipid (maleimide-DOBAQ, see below) was synthesized. By incorporating maleimide-DOBAQ into DOTAP:DOPC liposomes, cationic liposomes that are amenable to fusion and interbilayer crosslinking by anionic thiolated hyaluronic acid were generated. Free sulfhydryl moieties were introduced into hyaluronic acid polymers by the standard EDC chemistry with cysteine (total thiol content ~300 μmol/g of hyaluronic acid polymer as measured with Ellman's assay). Hyaluronic acid polymers modified with multiple sulfhydryl moieties are expected to serve as a multi-functional crosslinker by forming multiple intermolecular crosslinks between phospholipids (potentially >100 phospholipids, FIG. 8B), thus dramatically increasing serum stability of the particles.

Careful titration of thiolated hyaluronic acid polymer to maleimide-DOBAQ, combined with higher redox potential of cysteine in thiolated hyaluronic acid compared with DTT, allows encapsulation of proteins with minimal thiol-disulfide exchange (Redox potentials of DTT and cysteine are −0.33V and −0.24V, respectively, at pH 7, which corresponds to ~460-fold change in equilibrium constant, meaning that thiolated_hyaluronic acid is at least two orders of magnitude weaker reducing reagent than DTT). This indicates that conjugation of thiolated hyaluronic acid polymer to maleimide-DOBAQ is much more favorable than for it to reduce biomacromolecules. To examine whether Fab and Fc fragments are held together as intact IgG molecules via disulfide bonds, IgG are retrieved from MVPs and non-reducing SDS-PAGE and Coomassie blue staining is performed to check for IgG fragments.

Utilization of "Click" Cycloaddition to Form MVPs.

The alkyne-azide "click" cyclo addition is used to synthesize new MVPs (FIG. 8C). This "click" chemistry is bio-orthogonal to biomolecules including disulfide-containing proteins. Safe, copper-free, strain-promoted click chemistry between lipids modified with dibenzocyclooctyne (DBCO) and diazide is utilized. Next, IgG molecules are encapsulated into MVPs and the structural integrity of the IgG molecules is examined.

Multivalent Presentation of Biomacromolecules without Lipid Layers in MVPs.

Notably, one of the key advantages of MVPs is their ability to present multiple copies of biomacromoleules not only on the very outer surface but also throughout their multilamellar lipid layers, thereby allowing multivalent presentation of active cargo materials in a stable manner; even when some outer lipid layers peel off after initial contact with physiological condition, onion-like MPVs will permit multivalent presentation (FIG. 8D). Thus, in addition to encapsulation of IgG into MVPs (as above), the IgG molecules are displayed throughout the lipid layers in MVPs by adding introducing reactive thiols moieties into IgG molecules and conjugating them onto maleimide-DOBAQ on the lipid layers. This can be achieved by incubating IgG molecules with SATA, which will covalently modify primary amines in IgG into sulfhydryl group. By careful titration of IgG to SATA and subsequent interaction with maleimide-DOBAQ inserted lipid vesicles, IgG can be surface-conjugated onto liposomes and then fused/crosslinked with thiolated hyaluronic acid polymer (FIG. 8D).

Example 3

Synthesis of Maleimide-Modified DOBAQ (DOBAQ-MAL)

DOBAQ, EDC and NHS (1:1.5:1.5, m/m/m) were dissolved in DCM, stirred at RT for 0.5 h, followed by addition of 2-maleimidoethylamine and TEA (DOBAQ:MAL:TEA=1:1:10, m/m/m), and reaction at RT for 24 h. Product was purified by washing with 0.1 N HCl solution and saturated NaCl solution. DCM solvent was evaporated under nitrogen to obtain lipid films, which was further purified by washing with acetonitrile. Purified product was dissolved in chloroform at 10 mg/ml and stored at −80° C. The reaction scheme is shown in FIG. 9.

The product was identified by TLC and $^1$H-NMR. For TLC experiment, DOBAQ and DOBAQ-MAL were developed by chloroform, methanol, acetonitrile, and water (70:21:5:4, v/v/v/v), and stained with iodine gas. The product purity was quantified by HPLC. DOBAQ and DOBAQ-MAL of the same concentration were analyzed by HPLC using a diphenyl column, elution solution of water, methonal, acetonitrile, and trifluoroacetic acid (34.98:32.48:32.48:0.05, v/v/v/v), and detection wavelength of 220 nm.

The structure of DOBAQ-MAL was identified by $^1$H-NMR (FIG. 10) which showed the characteristic signal of hydrogen atoms in the maleimide group (~δ7.0).

As shown by TLC and HPLC results (FIG. 11), purity of DOBAQ-MAL was determined to be 91.1±0.6%

Example 4

Synthesis of DBCO-Modified DOPE (DOPE-DBCO)

DOPE, DBCO-NHS and triethylamine (1:1.2:1.2, m/m/m) were dissolved in DCM and stirred at RT overnight. Product was purified by washing with 0.1 N HCl solution and saturated NaCl solution. DCM solvent was evaporated under nitrogen to obtain lipid films, which was further purified by washing with acetonitrile. Purified product was dissolved in chloroform at 10 mg/ml and stored at −80° C. The reaction scheme is shown in FIG. 13.

Reaction product was identified by TLC and $^1$H-NMR. For TLC experiments, DOPE and DOPE-DBCO were developed by chloroform, methanol, acetonitrile, and water (75:16:5:4, v/v/v/v), and stained with iodine gas.

Figure 14:
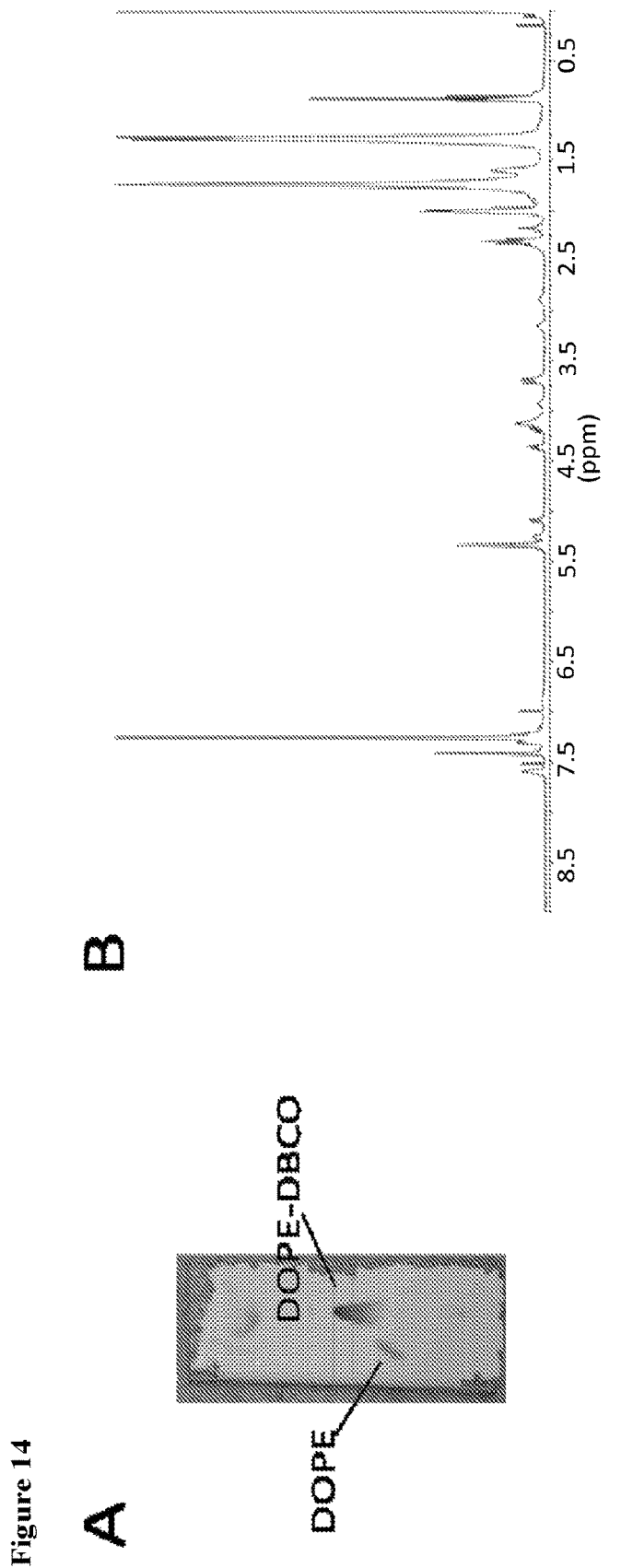
FIG. 14 shows identification of DOPE-DBCO. (A) TLC monitoring of the reaction. (B) $^1$H-NMR graph of the reaction product.

TLC results (FIG. 14A) showed successful conjugation of DBCO to DOPE. $^1$H-NMR result of the reaction product (FIG. 14B) showed appearance of characteristic signals of aromatic hydrogen atoms from the DBCO molecular structure (~δ7.5).

Example 5

Synthesis of Pegylated Azide-Modified Polyethylenimine (PEI-PEG$_4$-N$_3$)

Figure 15:
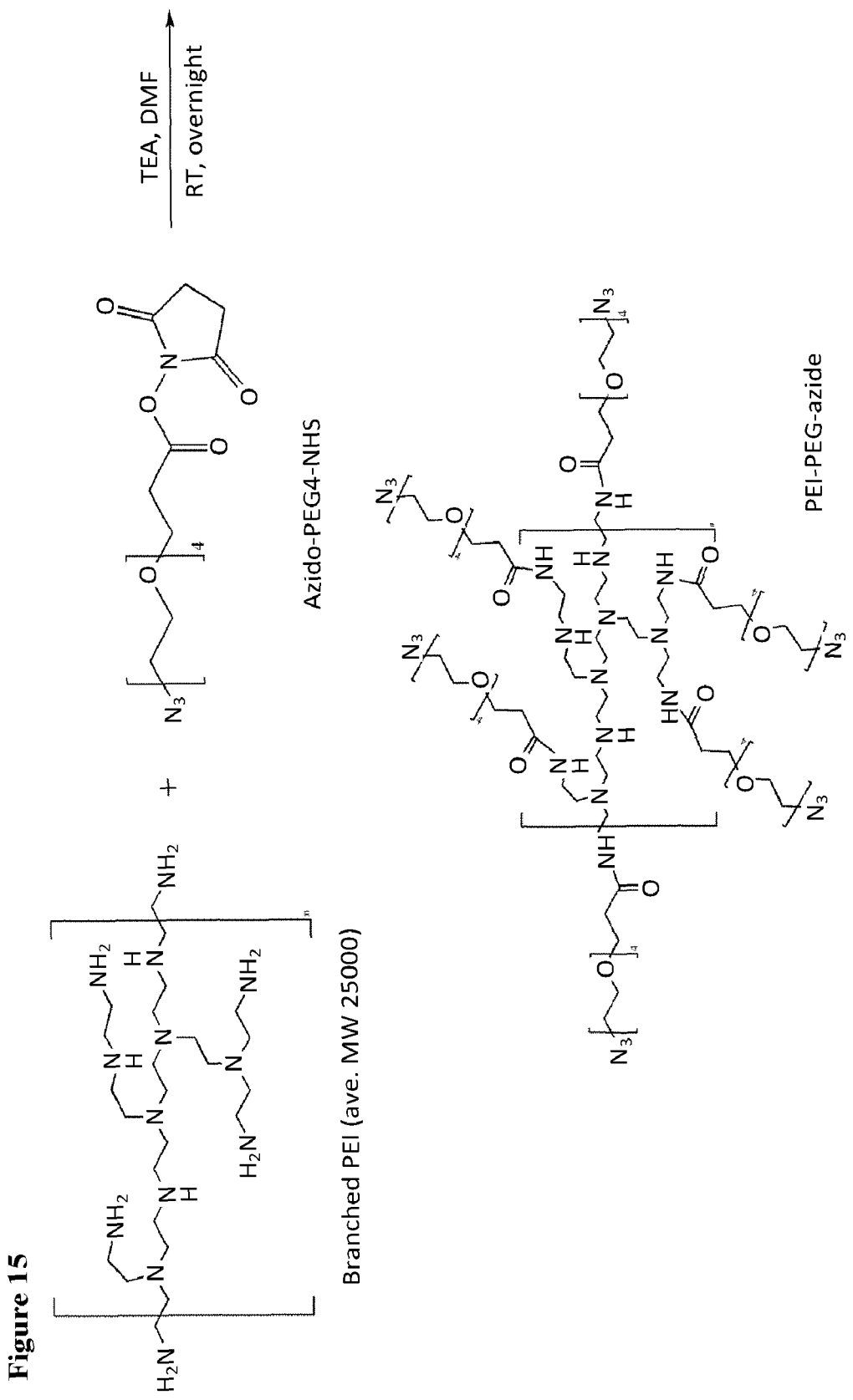
FIG. 15 shows synthesis scheme of PEI-PEG$_4$-N$_3$.

Branched PEI (average MW 25000), azido-PEG$_4$-NHS, and triethylamine (—NH$_2$:NHS:TEA=1:1.2:1.2, m/m/m) were dissolved in DMF and stirred at RT overnight. Product was purified by dialysis against ddH$_2$O for two days, followed by lyophilization. The reaction scheme is shown in FIG. 15.

Amount of azide groups in the product was quantified by labeling the product with fluorophore-conjugated DBCO. The amount of azido groups in the reaction product was calculated to be 2.99 mmol/g polymer.

Example 6

Lipid/Polymer Hybrid MVPs

This Example describes lipid/polymer hybrid MVPs composed of 1) DOBAQ-MAL reacted with HA-SH and 2) DOPE-DBCO reacted with PEI-azide.

For preparation of lipid/polymer hybrid MVPs cross-linked by maleimide/thiol groups, lipid films containing DOTAP, DOBAQ-MAL, and DOPC (50:25:25, m/m/m) were hydrated with PBS, followed by sonication to form unilamellar liposomes. HA-SH (100 μg/0.63 μmol lipids) w/ or w/o different adjuvants were added to liposomes (25 μg CpG, 50 μg polyI:C, or 20 μg MPLA/0.63 μmol lipids), followed by incubation at 37° C. for 1 h with constant shaking. Particles were washed by centrifuge (20817 g, 5 min) and PBS for 3 times to remove non-encapsulated adjuvants, resuspended in PBS, and sonicated briefly. Particles cross-linked by copper-free click chemistry were prepared similarly; lipid films containing DOPE-DBCO, DOPG, and DOPC (50:25:25, m/m/m) were hydrated with ddH$_2$O or BTP buffer (pH 7), followed by incubation with PEI-PEG$_4$-N$_3$ (100 μg/0.63 μmol lipids) at 37° C. for 2 h with constant shaking. Size and zeta potential of particles were measured by dynamic light scattering. Encapsulation efficiency (EE %) of MPLA, CpG, and poly I:C were measured by lipid recovery with a fluorophore-labeled lipid, UV absorbance at 260 nm, and a RNA quantification kit, respectively.

The resulting lipid/polymer hybrid nanoparticles displayed uniform size distribution (Table 2 and 3). Compared with unilamellar liposomes with the same lipid composition, particles cross-linked by HA-SH showed more than twice increase in size and switch of surface charges from positive to negative values.

TABLE 2

Characterization of lipid/polymer hybrid nanoparticles cross-linked by maleimide/thiol groups. Results are presented as mean ± SEM, n = 3.

| Hybrid MVPs formed with DOBAQ-MAL and HA-SH | Diameter (nm) | PDI | Zeta potential (mV) |
|---|---|---|---|
| Unilamellar liposomes | 108 ± 4 | 0.234 ± 0.04 | 20.3 ± 0.6 |
| HA-SH only | 254 ± 13 | 0.222 ± 0.03 | −16.4 ± 0.4 |
| MPLA/CpG | 268 ± 25 | 0.214 ± 0.03 | −18.5 ± 0.2 |
| Poly I:C | 315 ± 13 | 0.222 ± 0.01 | −18.5 ± 0.7 |

TABLE 3

Characterization of lipid/polymer hybrid nanoparticles cross-linked by copper-free click chemistry.

| Hybrid MVPs formed with DOPE-DBCO and PEI-PEG$_4$-N$_3$ | Diameter (nm) | PDI | Zeta potential (mV) |
|---|---|---|---|
| PEI-N$_3$ only | 436.7 | 0.092 | −28.7 |

A series of TLR agonists were encapsulated into the hybrid nanoparticle cross-linked by maleimide/thiol groups, with an average EE % of 88, 74, and 40 for MPLA, CpG, and poly I:C, respectively (Table 4).

TABLE 4

Encapsulation efficiency of TLR agonists in hybrid MVP nanoparticles cross-linked by maleimide/thiol groups. Results are presented as mean ± SEM, n = 3.

| EE % | MPLA | CpG | Poly I:C |
|---|---|---|---|
| MPLA/CpG | 88.1 ± 4 | 74.1 ± 6 | |
| Poly I:C | | | 39.8 ± 2 |

Example 7

MVPs Composed of DOPE-NHS Reacted with Branched PEI

Dried DOPC, DOPG, and DOPE-NHS (50:40:10, m/m/m) lipid films totaling 1.26 μmol were hydrated with 10 mM bis-tris propane buffer containing compound(s) of interest and sonicated to form unilamellar liposomes (ULVs). Addition of 2 kDa branched polyethyleneimine (PEI) solution (total 216 μg) to the ULV suspensions in a 1:1 molar ratio of estimated primary amines to NHS ester to produce MVPs composed of DOPE-NHS crosslinked with branched PEI. Produced MVP particles were incubation at 37° C. for one hour. Particles were washed by centrifugation (14000 g, 4 min, 4° C.) twice with endotoxin free water to remove unincorporated components and finally suspended in PBS and briefly sonicated. OVA and F1-V MVPs exhibited an average size of 280 nm±110 and 220 nm±75, respectively, with PDIs of 0.17 and 0.14, respectively. When 42 μg F1-V was used in the initial loading buffer, MVPs exhibited encapsulation efficiency of 12.8% as determined by Coomassie Blue staining of polyacrylamide gels.

Example 8

Conjugation of Adjuvants-Loaded MVP Nanoparticles to Surfaces of Tumor Cells

In order to test the effect of adjuvant delivery to dying tumor cells, adjuvant-loaded MVP nanoparticles were conjugated to dying tumor cells and examined their impact on immune responses. Excess maleimide groups from DOBAQ-MAL incorporated in adjuvants-loaded nanoparticles were utilized in order to achieve particle conjugation to free sulfhydryl groups of proteins on tumor cell membranes.

Tumor cells were treated ex vivo with mitoxantrone, an anthracycline chemodrug, followed by incubation with fluorophore-labeled, MPLA/CpG-co-loaded MVP nanoparticles at 4° C. for 12 h. Unconjugated particles were removed by centrifuge (1500 g, 5 min) and washed with PBS. Average number of particles conjugated on cell surfaces was calculated by fluorescence intensity recovered from the cell-particle conjugates and particle concentrations were measured by nanoparticle tracking analysis. The cell-particle conjugates were prepared freshly before use.

Figure 16:
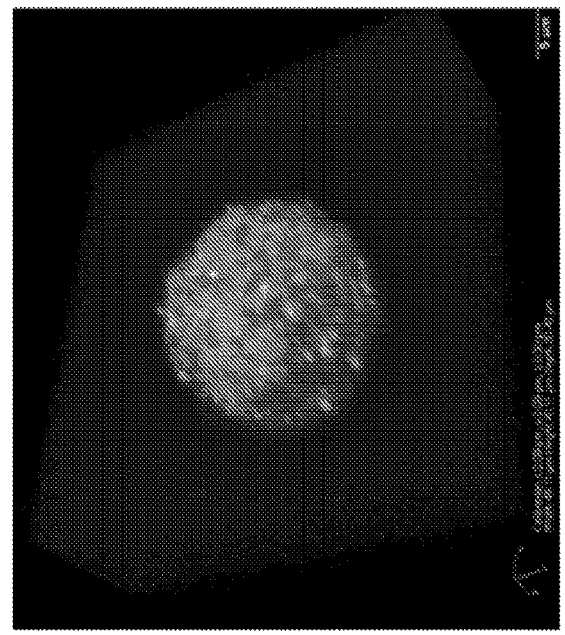
FIG. 16 shows conjugation of hybrid nanoparticles to surfaces of murine B16 melanoma cells. (A) Average number of conjugated particles per tumor cell as quantified by fluorophore-labeled particles and nanoparticle tracking analysis. (B) A representative confocal image of a cell-particle conjugate.
Figure 16:
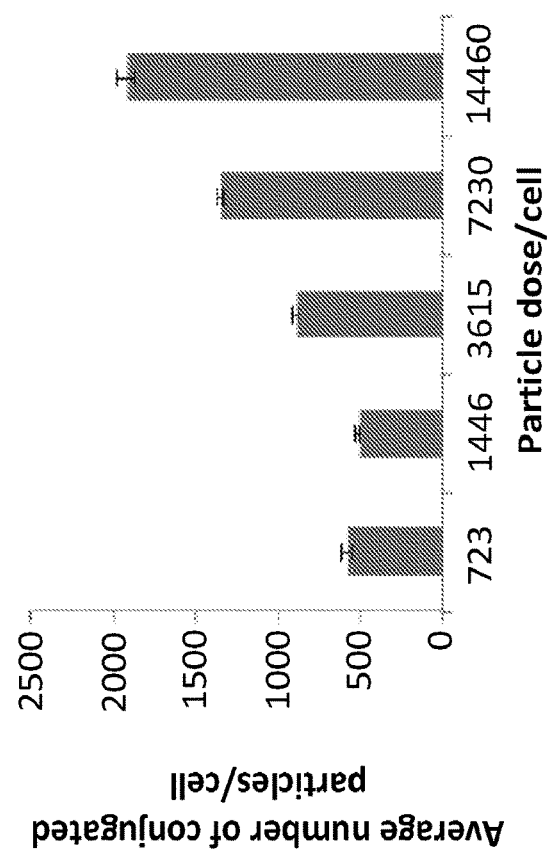

The average number of particles conjugated on cell surfaces increased with the ratio of particles to cells, reaching the peak value of ~2000 particles/cell (FIG. 16A). Most of conjugated particles were localized on surfaces of tumor cells, as shown by confocal images of cell-particle conjugates (FIG. 16B).

Use of Cell-Particle Conjugates as a Whole-Cell Cancer Vaccine

Immune responses after immunization with dying tumor cells surface-conjugated with adjuvant-loaded MVP nanoparticles were examined.

Murine bone marrow derived dendritic cells (BMDCs) were co-cultured with mitoxantrone-treated melanoma cells (Mit-B16OVA), tumor cells conjugated with adjuvants-loaded nanoparticles, or tumor cells supplemented with the same dose of soluble adjuvants (BMDCs:Mit-B16OVA=1:3) for one day, followed by measurement of tumor antigen-positive DCs using fluorophore-labeled tumor cells, maturation markers expressed in DCs by flow cytometry, and cytokines secreted by DCs in the co-culture supernatant by ELISA.

Figure 17:
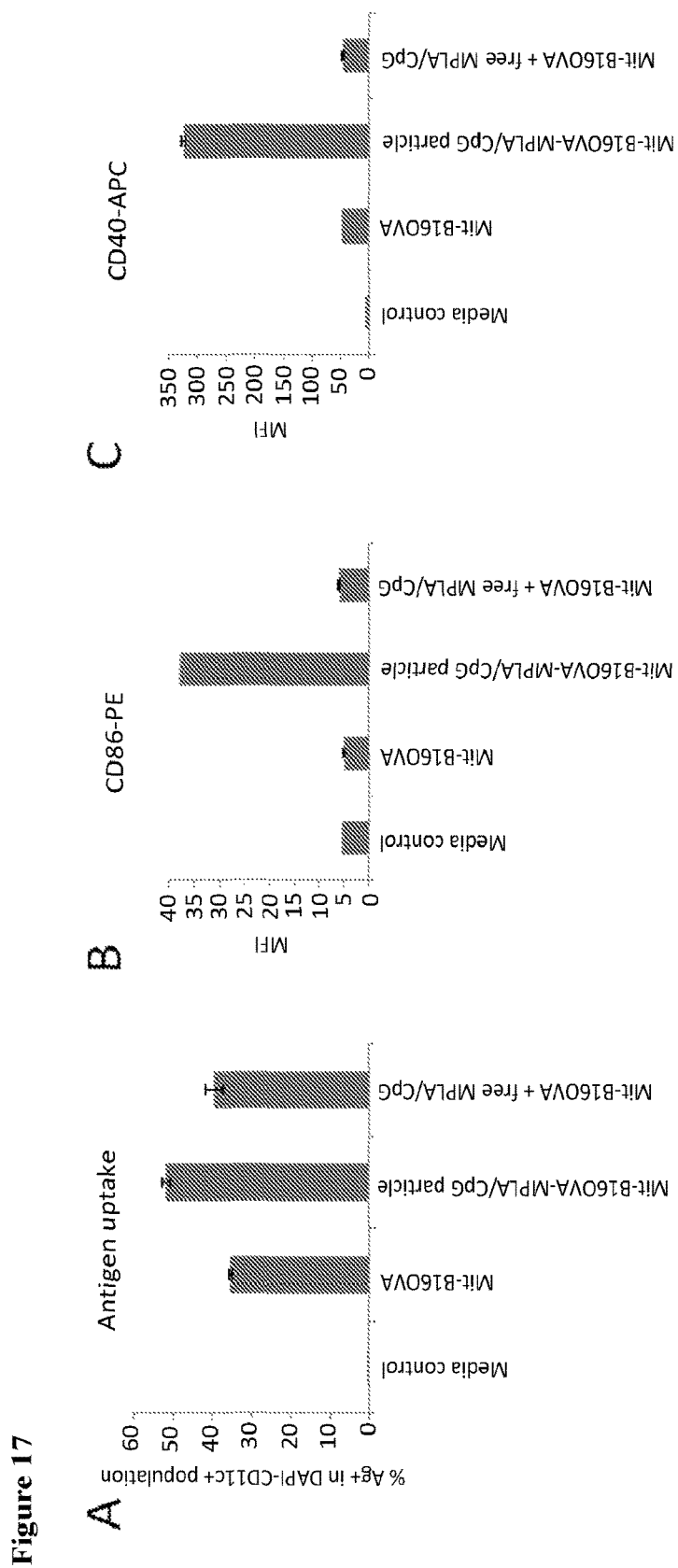
FIG. 17 shows activation of DCs by cell-particle conjugates. (A) DC uptake of fluorophore-labeled, mitoxantrone-treated melanoma cells conjugated with or without adjuvants-loaded nanoparticles, or admixed with soluble adjuvants. (B-C) Expression of co-stimulatory markers CD86 (B) and CD40 (C) on BMDCs. (D-F) Secretion of inflammatory cytokines including IL-12 (D), TNF-α (E), and IFN-γ (F) from BMDCs.
Figure 17:
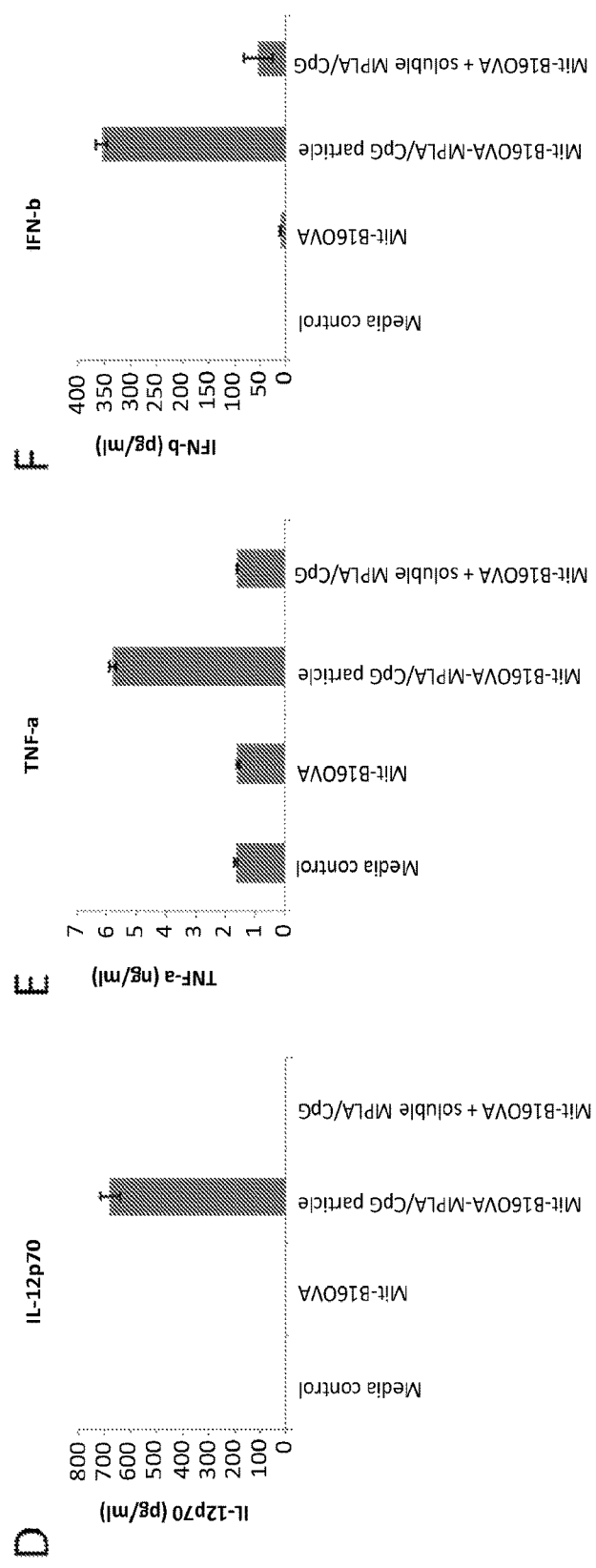

Uptake of tumor antigens by DCs was mainly driven by the presence of chemo-treated tumor cells, while conjugation of adjuvants-loaded particles increased antigen uptake by ~10% compared to chemo-treated tumor cells alone and those cells admixed with the same dose of soluble adjuvants (FIG. 17A). Cell-particle conjugates significantly up-regulated co-stimulatory markers including CD86 (FIG. 17B) and CD40 (FIG. 17C) on DCs. Cell-particle conjugates also promoted BMDCs to secrete high levels of IL-12 (FIG. 17D), TNF-α (FIG. 17E), and IFN-γ (FIG. 17F), further demonstrating the activation of DCs by dying tumor cells presenting MPLA/CpG adjuvants on their surfaces.

Tumor Antigen-Specific Immune Responses In Vivo

Female BABL/c mice (n=5 per group) were immunized subcutaneously with PBS, one or two doses of mitoxantrone-treated colon carcinoma CT26 cells that were conjugated with MPLA/CpG-loaded nanoparticles (four million chemo-treated tumor cells/mouse). Animals were then challenged with 2E5 live CT26 cells/mouse on day 14 after the last immunization. Tumor growth and animal survival were monitored.

Figure 18:
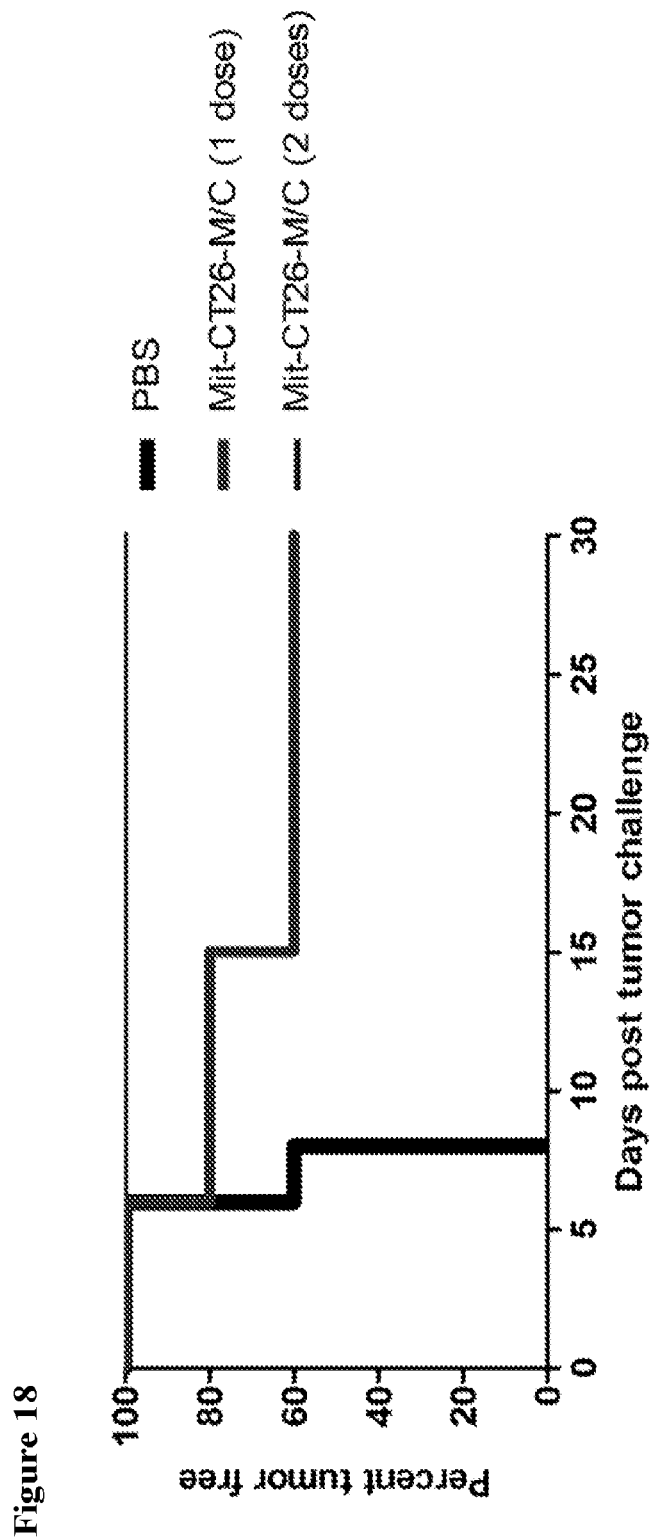
FIG. 18 shows anti-tumor immune responses elicited by cell-particle conjugates.

The CT26 cell-particle conjugates elicited robust anti-tumor immune responses and protected 60% and 100% of animals with one and two vaccination doses, respectively, against live CT26 tumor challenge (FIG. 18).

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A composition, comprising:
   A molecule encapsulated in a multilamellar lipid vesicle comprising covalent crosslinks between lipid bilayers comprising one or more functionalized lipids, wherein at least two lipid bilayers in the multilamellar lipid vesicle are covalently crosslinked to each other by thiolated hyaluronic acid.

2. The composition of claim 1, wherein said one or more lipids are selected from the group consisting of DOTAP, DOPE, DOBAQ, and DOPC.

3. The composition of claim 1, wherein said one or more lipid are maleimide-functionalized or modified with dibenzocyclooctyne (DBCO).

4. The composition of claim 1, wherein said thiolated hyaluronic acid comprises multiple sulfhydryl moieties.

5. A method of delivering a molecule to a subject, comprising:
   administering or a molecule encapsulated in a multilamellar lipid vesicle comprising covalent crosslinks between lipid bilayers, wherein at least two lipid bilayers in the multilamellar lipid vesicle are covalently crosslinked to each other by thiolated hyaluronic acid to a subject.

6. The method of claim 5, wherein said molecule is an antigen and said administering induces an immune response to said antigen in said subject.

7. The method of claim 6, wherein said immune response induces immunity against a pathogen.

8. The method of claim 6, wherein said antigen is a tumor antigen.

* * * * *